(12) United States Patent
Usuda et al.

(10) Patent No.: US 7,026,149 B2
(45) Date of Patent: Apr. 11, 2006

(54) **POLYNUCLEOTIDES ENCODING POLYPEPTIDES INVOLVED IN THE STRESS RESPONSE TO ENVIRONMENTAL CHANGES IN *METHYLOPHILUS METHYLOTROPHUS***

(75) Inventors: Yoshihiro Usuda, Kawasaki (JP);
Yousuke Nishio, Kawasaki (JP);
Hisashi Yasueda, Kawasaki (JP);
Shinichi Sugimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 49 days.

(21) Appl. No.: 10/375,010

(22) Filed: Feb. 28, 2003

(65) Prior Publication Data
US 2004/0170985 A1    Sep. 2, 2004

(51) Int. Cl.
*C12N 9/12*    (2006.01)
*C07K 1/00*    (2006.01)
(52) U.S. Cl. .................. 435/194; 435/183; 435/252.3; 435/320.1; 530/350; 536/23.1; 536/23.2
(58) Field of Classification Search ................ 435/194, 435/183, 257.3, 320.1, 6; 536/23.1, 23.2
See application file for complete search history.

(56) References Cited

U.S. PATENT DOCUMENTS

| | | | |
|---|---|---|---|
| 2004/0091891 A1 | 5/2004 | Yomantas et al. | 435/6 |
| 2004/0170986 A1 | 9/2004 | Usuda et al. | 435/6 |
| 2004/0170987 A1 | 9/2004 | Usuda et al. | 435/6 |

FOREIGN PATENT DOCUMENTS

| | | |
|---|---|---|
| EP | 0035831 | 9/1981 |
| EP | 0037273 | 10/1981 |
| EP | 0066994 | 12/1982 |
| EP | 1188822 | 3/2002 |
| WO | WO 02/38777 | 5/2002 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
U.S. Appl. No. 09/926,299, filed Oct. 9, 2001, Gunji et al.

* cited by examiner

*Primary Examiner*—Richard Hutson
(74) *Attorney, Agent, or Firm*—Cermak & Kenealy, LLP; Shelly Guest Cermak

(57) ABSTRACT

The present invention provides polypeptides and polynucleotides involved in the stress response to environmental changes in *Methylophilus methylotrophus* and methods of producing amino acids in microorganisms having enhanced or attenuated expression of these polypeptides and/or polynucleotides.

20 Claims, No Drawings

SEQUENCE LISTING

<160> NUMBER OF SEQ ID NOS: 34

<210> SEQ ID NO 1
<211> LENGTH: 543
<212> TYPE: DNA
<213> ORGANISM: Methylophilus methylotrophus
<220> FEATURE:
<221> NAME/KEY: CDS
<222> LOCATION: (1)..(543)
<223> OTHER INFORMATION:

<400> SEQUENCE: 1

| | | | | | | | | | | | | | | | | |
|---|---|---|---|---|---|---|---|---|---|---|---|---|---|---|---|---|
| gtg | ggt | ccc | aag | tcg | tcc | aca | cgc | atg | gct | tat | cac | ctc | ctg | cag | cgg | 48 |
| Val | Gly | Pro | Lys | Ser | Ser | Thr | Arg | Met | Ala | Tyr | His | Leu | Leu | Gln | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gac | aga | gaa | ggt | gcg | caa | aaa | ctg | gct | gcg | agt | ttg | cag | cag | gcg | ctg | 96 |
| Asp | Arg | Glu | Gly | Ala | Gln | Lys | Leu | Ala | Ala | Ser | Leu | Gln | Gln | Ala | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| gac | aag | ctc | gct | cat | tgt | gat | tat | tgc | aat | aac | ttc | agc | gaa | cac | cag | 144 |
| Asp | Lys | Leu | Ala | His | Cys | Asp | Tyr | Cys | Asn | Asn | Phe | Ser | Glu | His | Gln | |
| | | | | 35 | | | | | 40 | | | | | 45 | | |

| | | | | | | | | | | | | | | | | |
|---|---|---|---|---|---|---|---|---|---|---|---|---|---|---|---|---|
| gta | tgt | agt | gtg | tgc | ctg | gaa | acc | agc | cgt | gac | aaa | tca | acg | cta | tgc | 192 |
| Val | Cys | Ser | Val | Cys | Leu | Glu | Thr | Ser | Arg | Asp | Lys | Ser | Thr | Leu | Cys | |
| 50 | | | | | 55 | | | | | 60 | | | | | | |

| | | | | | | | | | | | | | | | | |
|---|---|---|---|---|---|---|---|---|---|---|---|---|---|---|---|---|
| gtg | gtc | gaa | atg | cct | acc | gac | ctc | atg | atg | ctg | gaa | aac | acc | cgc | agt | 240 |
| Val | Val | Glu | Met | Pro | Thr | Asp | Leu | Met | Met | Leu | Glu | Asn | Thr | Arg | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tac | caa | ggt | caa | tat | ttt | gta | ctg | atg | ggc | aaa | cta | tcg | ccc | atg | gat | 288 |
| Tyr | Gln | Gly | Gln | Tyr | Phe | Val | Leu | Met | Gly | Lys | Leu | Ser | Pro | Met | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| ggt | ata | gga | ccc | aaa | gat | att | cat | ctc | gat | aaa | ctg | ctc | aag | cgc | gcg | 336 |
| Gly | Ile | Gly | Pro | Lys | Asp | Ile | His | Leu | Asp | Lys | Leu | Leu | Lys | Arg | Ala | |
| | | | | 100 | | | | | 105 | | | | | 110 | | |

| | | | | | | | | | | | | | | | | |
|---|---|---|---|---|---|---|---|---|---|---|---|---|---|---|---|---|
| caa | gat | acc | gcc | att | cat | gaa | gtc | atc | ctg | gcc | acc | aat | ttc | acc | tcc | 384 |
| Gln | Asp | Thr | Ala | Ile | His | Glu | Val | Ile | Leu | Ala | Thr | Asn | Phe | Thr | Ser | |
| | | | | 115 | | | | | 120 | | | | | 125 | | |

| | | | | | | | | | | | | | | | | |
|---|---|---|---|---|---|---|---|---|---|---|---|---|---|---|---|---|
| gag | ggc | gaa | gcc | aca | gcc | cac | tat | ata | gga | cag | atg | ctc | aaa | tca | cgt | 432 |
| Glu | Gly | Glu | Ala | Thr | Ala | His | Tyr | Ile | Gly | Gln | Met | Leu | Lys | Ser | Arg | |
| | | 130 | | | | | 135 | | | | | 140 | | | | |

| | | | | | | | | | | | | | | | | |
|---|---|---|---|---|---|---|---|---|---|---|---|---|---|---|---|---|
| ggc | atc | cgt | gtg | agc | cgg | att | gcc | cgc | ggc | tta | cct | atg | ggt | gga | gaa | 480 |
| Gly | Ile | Arg | Val | Ser | Arg | Ile | Ala | Arg | Gly | Leu | Pro | Met | Gly | Gly | Glu | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| att | gag | tac | gtc | gac | agc | ggc | acc | ctc | tcg | aca | gcc | ctg | ctg | gaa | cgc | 528 |
| Ile | Glu | Tyr | Val | Asp | Ser | Gly | Thr | Leu | Ser | Thr | Ala | Leu | Leu | Glu | Arg | |
| | | | | 165 | | | | | 170 | | | | | 175 | | |

| | | | | |
|---|---|---|---|---|
| aag | gtt | tta | act | tag | 543 |
| Lys | Val | Leu | Thr | | |
| | | | 180 | | |

<210> SEQ ID NO 2
<211> LENGTH: 180
<212> TYPE: PRT
<213> ORGANISM: Methylophilus methylotrophus

<400> SEQUENCE: 2

Val Gly Pro Lys Ser Ser Thr Arg Met Ala Tyr His Leu Leu Gln Arg
1               5                   10                  15

Asp Arg Glu Gly Ala Gln Lys Leu Ala Ala Ser Leu Gln Gln Ala Leu
            20                  25                  30

Asp Lys Leu Ala His Cys Asp Tyr Cys Asn Asn Phe Ser Glu His Gln

```
                    35                  40                  45
Val Cys Ser Val Cys Leu Glu Thr Ser Arg Asp Lys Ser Thr Leu Cys
 50                  55                  60

Val Val Glu Met Pro Thr Asp Leu Met Met Leu Glu Asn Thr Arg Ser
 65                  70                  75                  80

Tyr Gln Gly Gln Tyr Phe Val Leu Met Gly Lys Leu Ser Pro Met Asp
                 85                  90                  95

Gly Ile Gly Pro Lys Asp Ile His Leu Asp Lys Leu Leu Lys Arg Ala
                100                 105                 110

Gln Asp Thr Ala Ile His Glu Val Ile Leu Ala Thr Asn Phe Thr Ser
            115                 120                 125

Glu Gly Glu Ala Thr Ala His Tyr Ile Gly Gln Met Leu Lys Ser Arg
130                 135                 140

Gly Ile Arg Val Ser Arg Ile Ala Arg Gly Leu Pro Met Gly Gly Glu
145                 150                 155                 160

Ile Glu Tyr Val Asp Ser Gly Thr Leu Ser Thr Ala Leu Leu Glu Arg
                165                 170                 175

Lys Val Leu Thr
            180

<210> SEQ ID NO 3
<211> LENGTH: 1659
<212> TYPE: DNA
<213> ORGANISM: Methylophilus methylotrophus
<220> FEATURE:
<221> NAME/KEY: CDS
<222> LOCATION: (1)..(1659)
<223> OTHER INFORMATION:

<400> SEQUENCE: 3 atg cta caa gcc ctt tct atc cga gac ttt gtc att gtt gat acg ctg      48
Met Leu Gln Ala Leu Ser Ile Arg Asp Phe Val Ile Val Asp Thr Leu
  1               5                  10                  15 gaa ctt gag ttc tca gca gga tac acc gca ctc act ggt gag acg ggt      96
Glu Leu Glu Phe Ser Ala Gly Tyr Thr Ala Leu Thr Gly Glu Thr Gly
             20                  25                  30 gcg ggt aaa tcc atc ctc att gat gcc ctg tct tta agc ctg ggc gca     144
Ala Gly Lys Ser Ile Leu Ile Asp Ala Leu Ser Leu Ser Leu Gly Ala
         35                  40                  45 cgt aac gag ggg gat gtg acg cgc aag ggc tgt gaa aag gcg gaa atc     192
Arg Asn Glu Gly Asp Val Thr Arg Lys Gly Cys Glu Lys Ala Glu Ile
 50                  55                  60 tca acg act ttt gat att gcg gat aat ctg gca gcc cgg gat tgg cta     240
Ser Thr Thr Phe Asp Ile Ala Asp Asn Leu Ala Ala Arg Asp Trp Leu
 65                  70                  75                  80 cag gca caa gaa atc gat att gag gat gcc ctg gta ttg cgc cgt gtg     288
Gln Ala Gln Glu Ile Asp Ile Glu Asp Ala Leu Val Leu Arg Arg Val
                 85                  90                  95 att tat gcc gat ggc cgt agc cgc gcc ttt att aat ggt gcc tcg gca     336
Ile Tyr Ala Asp Gly Arg Ser Arg Ala Phe Ile Asn Gly Ala Ser Ala
                100                 105                 110 acg gta ggc caa ttg cgc gaa atc ggc gaa acc ctc att gat att tat     384
Thr Val Gly Gln Leu Arg Glu Ile Gly Glu Thr Leu Ile Asp Ile Tyr
            115                 120                 125 agc cag aat gcg cat cac tcc tta ctc aaa att gct acc cag cgc gag     432
Ser Gln Asn Ala His His Ser Leu Leu Lys Ile Ala Thr Gln Arg Glu
130                 135                 140 atc ctg gat gct tat gca caa gcg tca cca ctg gca aaa caa gtt gcc     480
Ile Leu Asp Ala Tyr Ala Gln Ala Ser Pro Leu Ala Lys Gln Val Ala
```

-continued

```
                145                 150                 155                 160
aag tta tac aac gac tgg ttt cag cta cat cag cag cag ctg gcg tat      528
Lys Leu Tyr Asn Asp Trp Phe Gln Leu His Gln Gln Gln Leu Ala Tyr
                    165                 170                 175 gag aaa aat tcc agc cag ttt gca gaa gag ctg gct gag cta cgt gac      576
Glu Lys Asn Ser Ser Gln Phe Ala Glu Glu Leu Ala Glu Leu Arg Asp
                    180                 185                 190 agt aca aga gaa ttg aag cag ttg ggt ttt gcc agt gac gaa tgg cag      624
Ser Thr Arg Glu Leu Lys Gln Leu Gly Phe Ala Ser Asp Glu Trp Gln
                195                 200                 205 gca tta cag cag gag cat gtc cgt tta agt aac ggt gcc agt ttg ctc      672
Ala Leu Gln Gln Glu His Val Arg Leu Ser Asn Gly Ala Ser Leu Leu
            210                 215                 220 agt ggc atg gaa gcc agc ctg caa atg atg agt gaa ggg gat gaa gtc      720
Ser Gly Met Glu Ala Ser Leu Gln Met Met Ser Glu Gly Asp Glu Val
225                 230                 235                 240 aat gcg ctg gat ttg ctc tcc cag gca caa acc aag ctg gcc gaa ctg      768
Asn Ala Leu Asp Leu Leu Ser Gln Ala Gln Thr Lys Leu Ala Glu Leu
                    245                 250                 255 cag acg atg gat gcc gga ttg caa gcg att gct gaa aac ctt gat tca      816
Gln Thr Met Asp Ala Gly Leu Gln Ala Ile Ala Glu Asn Leu Asp Ser
                    260                 265                 270 gcc gtg gtg caa ctg gaa gaa gcc agc cgg gca ctg aat cgc tat ctg      864
Ala Val Val Gln Leu Glu Glu Ala Ser Arg Ala Leu Asn Arg Tyr Leu
                275                 280                 285 caa aaa agt gag ctg gat cct gaa cgc ctc gct gag gtt gaa gcg cgt      912
Gln Lys Ser Glu Leu Asp Pro Glu Arg Leu Ala Glu Val Glu Ala Arg
            290                 295                 300 atc cag gcg att cat ggc gcc gca cgc aag ttc cgc atc aag cct gat      960
Ile Gln Ala Ile His Gly Ala Ala Arg Lys Phe Arg Ile Lys Pro Asp
305                 310                 315                 320 gag ctg cct gaa tta ttg gcc cag caa ttg cag cgg gtg gct gag ctt     1008
Glu Leu Pro Glu Leu Leu Ala Gln Gln Leu Gln Arg Val Ala Glu Leu
                    325                 330                 335 gaa ggt ttt tct gat gac ggt gcc ttg gcc aag caa gtg caa cta gcc     1056
Glu Gly Phe Ser Asp Asp Gly Ala Leu Ala Lys Gln Val Gln Leu Ala
                    340                 345                 350 tgg aaa gcc tac cat gaa caa gcc acc cag ctt tcg tca gcc agg cag     1104
Trp Lys Ala Tyr His Glu Gln Ala Thr Gln Leu Ser Ser Ala Arg Gln
                355                 360                 365 caa gct gcg caa aga ctg gct aaa acc atc act gag caa atg cag gcg     1152
Gln Ala Ala Gln Arg Leu Ala Lys Thr Ile Thr Glu Gln Met Gln Ala
            370                 375                 380 ttg tcc tta aag ggc ggc cag ttt gct gtg gct tta aca acc tcc agt     1200
Leu Ser Leu Lys Gly Gly Gln Phe Ala Val Ala Leu Thr Thr Ser Ser
385                 390                 395                 400 gag ccc act gct cat gga ttg gaa caa gtg gag ttc ctg gtg gct ggt     1248
Glu Pro Thr Ala His Gly Leu Glu Gln Val Glu Phe Leu Val Ala Gly
                    405                 410                 415 cat gcc ggc gtt gag ccc cgt ccg ctc aat aaa gtt gcc tct ggt ggt     1296
His Ala Gly Val Glu Pro Arg Pro Leu Asn Lys Val Ala Ser Gly Gly
                    420                 425                 430 gag ttg tca cgc atc agc ctg gcc ttg cag gtg acc acc gct tca tta     1344
Glu Leu Ser Arg Ile Ser Leu Ala Leu Gln Val Thr Thr Ala Ser Leu
                435                 440                 445 ggc aca gtg ccc tgc atg att ttt gat gaa gtg gat gtt ggc att ggc     1392
Gly Thr Val Pro Cys Met Ile Phe Asp Glu Val Asp Val Gly Ile Gly
            450                 455                 460 ggc ggc gtt gca gaa gtg gtg ggc aga ttg ttg aat cag ctt ggc cag     1440
```

```
Gly Gly Val Ala Glu Val Val Gly Arg Leu Leu Asn Gln Leu Gly Gln
465                 470                 475                 480 cat cgg cag gta ctg gtg att acc cac ctg gca caa gtt gca gca cag    1488
His Arg Gln Val Leu Val Ile Thr His Leu Ala Gln Val Ala Ala Gln
                485                 490                 495 gcg cag cag cat ttg cag gtt agc aaa tct gag cag caa ggc gcg aca    1536
Ala Gln Gln His Leu Gln Val Ser Lys Ser Glu Gln Gln Gly Ala Thr
            500                 505                 510 tta agc cgt att cgc gca ttg gac gca agc gag cga gta gaa gag gtg    1584
Leu Ser Arg Ile Arg Ala Leu Asp Ala Ser Glu Arg Val Glu Glu Val
        515                 520                 525 gca cgt atg cta ggt ggt ttg cag att act gag acg aca agg aat cac    1632
Ala Arg Met Leu Gly Gly Leu Gln Ile Thr Glu Thr Thr Arg Asn His
    530                 535                 540 gcc cgg gaa atg ctt ggg ata gtc tga                                1659
Ala Arg Glu Met Leu Gly Ile Val
545                 550

<210> SEQ ID NO 4
<211> LENGTH: 552
<212> TYPE: PRT
<213> ORGANISM: Methylophilus methylotrophus

<400> SEQUENCE: 4

Met Leu Gln Ala Leu Ser Ile Arg Asp Phe Val Ile Val Asp Thr Leu
1               5                   10                  15

Glu Leu Glu Phe Ser Ala Gly Tyr Thr Ala Leu Thr Gly Glu Thr Gly
            20                  25                  30

Ala Gly Lys Ser Ile Leu Ile Asp Ala Leu Ser Leu Ser Leu Gly Ala
        35                  40                  45

Arg Asn Glu Gly Asp Val Thr Arg Lys Gly Cys Glu Lys Ala Glu Ile
    50                  55                  60

Ser Thr Thr Phe Asp Ile Ala Asp Asn Leu Ala Ala Arg Asp Trp Leu
65                  70                  75                  80

Gln Ala Gln Glu Ile Asp Ile Glu Asp Ala Leu Val Leu Arg Arg Val
                85                  90                  95

Ile Tyr Ala Asp Gly Arg Ser Arg Ala Phe Ile Asn Gly Ala Ser Ala
            100                 105                 110

Thr Val Gly Gln Leu Arg Glu Ile Gly Glu Thr Leu Ile Asp Ile Tyr
        115                 120                 125

Ser Gln Asn Ala His His Ser Leu Leu Lys Ile Ala Thr Gln Arg Glu
    130                 135                 140

Ile Leu Asp Ala Tyr Ala Gln Ala Ser Pro Leu Ala Lys Gln Val Ala
145                 150                 155                 160

Lys Leu Tyr Asn Asp Trp Phe Gln Leu His Gln Gln Leu Ala Tyr
                165                 170                 175

Glu Lys Asn Ser Ser Gln Phe Ala Glu Glu Leu Ala Glu Leu Arg Asp
            180                 185                 190

Ser Thr Arg Glu Leu Lys Gln Leu Gly Phe Ala Ser Asp Glu Trp Gln
        195                 200                 205

Ala Leu Gln Gln Glu His Val Arg Leu Ser Asn Gly Ala Ser Leu Leu
    210                 215                 220

Ser Gly Met Glu Ala Ser Leu Gln Met Met Ser Glu Gly Asp Glu Val
225                 230                 235                 240

Asn Ala Leu Asp Leu Leu Ser Gln Ala Gln Thr Lys Leu Ala Glu Leu
                245                 250                 255
```

```
Gln Thr Met Asp Ala Gly Leu Gln Ala Ile Ala Glu Asn Leu Asp Ser
            260                 265                 270

Ala Val Val Gln Leu Glu Glu Ala Ser Arg Ala Leu Asn Arg Tyr Leu
        275                 280                 285

Gln Lys Ser Glu Leu Asp Pro Glu Arg Leu Ala Glu Val Glu Ala Arg
    290                 295                 300

Ile Gln Ala Ile His Gly Ala Ala Arg Lys Phe Arg Ile Lys Pro Asp
305                 310                 315                 320

Glu Leu Pro Glu Leu Leu Ala Gln Gln Leu Gln Arg Val Ala Glu Leu
                325                 330                 335

Glu Gly Phe Ser Asp Asp Gly Ala Leu Ala Lys Gln Val Gln Leu Ala
            340                 345                 350

Trp Lys Ala Tyr His Glu Gln Ala Thr Gln Leu Ser Ser Ala Arg Gln
        355                 360                 365

Gln Ala Ala Gln Arg Leu Ala Lys Thr Ile Thr Glu Gln Met Gln Ala
    370                 375                 380

Leu Ser Leu Lys Gly Gly Gln Phe Ala Val Ala Leu Thr Thr Ser Ser
385                 390                 395                 400

Glu Pro Thr Ala His Gly Leu Glu Gln Val Glu Phe Leu Val Ala Gly
                405                 410                 415

His Ala Gly Val Glu Pro Arg Pro Leu Asn Lys Val Ala Ser Gly Gly
            420                 425                 430

Glu Leu Ser Arg Ile Ser Leu Ala Leu Gln Val Thr Thr Ala Ser Leu
        435                 440                 445

Gly Thr Val Pro Cys Met Ile Phe Asp Glu Val Asp Val Gly Ile Gly
    450                 455                 460

Gly Gly Val Ala Glu Val Val Gly Arg Leu Leu Asn Gln Leu Gly Gln
465                 470                 475                 480

His Arg Gln Val Leu Val Ile Thr His Leu Ala Gln Val Ala Ala Gln
                485                 490                 495

Ala Gln Gln His Leu Gln Val Ser Lys Ser Glu Gln Gln Gly Ala Thr
            500                 505                 510

Leu Ser Arg Ile Arg Ala Leu Asp Ala Ser Glu Arg Val Glu Glu Val
        515                 520                 525

Ala Arg Met Leu Gly Gly Leu Gln Ile Thr Glu Thr Thr Arg Asn His
    530                 535                 540

Ala Arg Glu Met Leu Gly Ile Val
545                 550

<210> SEQ ID NO 5
<211> LENGTH: 753
<212> TYPE: DNA
<213> ORGANISM: Methylophilus methylotrophus
<220> FEATURE:
<221> NAME/KEY: CDS
<222> LOCATION: (1)..(753)
<223> OTHER INFORMATION:

<400> SEQUENCE: 5 atg gca cta aaa cca tct gat tca ggt agc cac aaa caa agc ctg caa    48
Met Ala Leu Lys Pro Ser Asp Ser Gly Ser His Lys Gln Ser Leu Gln
1               5                   10                  15 ccg gtt ttt att ctt cat acc tat ccc ttt aag gaa acc agc ctg gtc    96
Pro Val Phe Ile Leu His Thr Tyr Pro Phe Lys Glu Thr Ser Leu Val
                20                  25                  30 gtc gaa atg ttt agt cgc gac ctg gga cgt att gcg gcc gtt gcc aag   144
Val Glu Met Phe Ser Arg Asp Leu Gly Arg Ile Ala Ala Val Ala Lys
```

```
            35                  40                  45
ggt gca cga cgg ccc ctg tcg gcc atg cgt ggc atg ttg cag tct ttt      192
Gly Ala Arg Arg Pro Leu Ser Ala Met Arg Gly Met Leu Gln Ser Phe
        50                  55                  60 cag cag ctg gcc ggt acc tgg tca ggc aaa aac gag ctc aaa acc ctg      240
Gln Gln Leu Ala Gly Thr Trp Ser Gly Lys Asn Glu Leu Lys Thr Leu
65                  70                  75                  80 cat gac ctc gag tgg atg aca ggc ctg aca ttg ctc agg ggc gat gcg      288
His Asp Leu Glu Trp Met Thr Gly Leu Thr Leu Leu Arg Gly Asp Ala
                85                  90                  95 ctc atg tgc ggt ttt tac atg aac gag ctg ttg ctg cgc ttg ctg ccg      336
Leu Met Cys Gly Phe Tyr Met Asn Glu Leu Leu Leu Arg Leu Leu Pro
            100                 105                 110 cgg gat gat gcc cat acg cag cta ttc gag tat tac gcc caa acc att      384
Arg Asp Asp Ala His Thr Gln Leu Phe Glu Tyr Tyr Ala Gln Thr Ile
        115                 120                 125 caa tta ttg tct acc ttg cag cag gat gcc ggc agt ggc cag ctg gcc      432
Gln Leu Leu Ser Thr Leu Gln Gln Asp Ala Gly Ser Gly Gln Leu Ala
    130                 135                 140 gag atc atg cgc cgg ttt gaa ctc aaa atg tta cag gaa ttg ggg tac      480
Glu Ile Met Arg Arg Phe Glu Leu Lys Met Leu Gln Glu Leu Gly Tyr
145                 150                 155                 160 gcg gta cca ctg acg cac gat gaa cat ggc gaa gtg ata cac gcc gat      528
Ala Val Pro Leu Thr His Asp Glu His Gly Glu Val Ile His Ala Asp
                165                 170                 175 gag ata tac cgc ttt gag gcc gac tat ggc gca tgt gcc ccg tct gca      576
Glu Ile Tyr Arg Phe Glu Ala Asp Tyr Gly Ala Cys Ala Pro Ser Ala
            180                 185                 190 acc aga aat ggg ttg ctg gtg cag ggg gca aca tta ctg gag atg gcc      624
Thr Arg Asn Gly Leu Leu Val Gln Gly Ala Thr Leu Leu Glu Met Ala
        195                 200                 205 cgc ggc aat tac agc agc gcc acg acg caa tca caa agc aag caa ctc      672
Arg Gly Asn Tyr Ser Ser Ala Thr Thr Gln Ser Gln Ser Lys Gln Leu
    210                 215                 220 atg cgt tac ctg cta cag cat tac ctg ggt gaa aaa ccc ttg cat acg      720
Met Arg Tyr Leu Leu Gln His Tyr Leu Gly Glu Lys Pro Leu His Thr
225                 230                 235                 240 cgg caa ctg ctg gtg gat ttg cag gat ttc tga                          753
Arg Gln Leu Leu Val Asp Leu Gln Asp Phe
                245                 250

<210> SEQ ID NO 6
<211> LENGTH: 250
<212> TYPE: PRT
<213> ORGANISM: Methylophilus methylotrophus

<400> SEQUENCE: 6

Met Ala Leu Lys Pro Ser Asp Ser Gly Ser His Lys Gln Ser Leu Gln
1               5                   10                  15

Pro Val Phe Ile Leu His Thr Tyr Pro Phe Lys Glu Thr Ser Leu Val
            20                  25                  30

Val Glu Met Phe Ser Arg Asp Leu Gly Arg Ile Ala Ala Val Ala Lys
        35                  40                  45

Gly Ala Arg Arg Pro Leu Ser Ala Met Arg Gly Met Leu Gln Ser Phe
    50                  55                  60

Gln Gln Leu Ala Gly Thr Trp Ser Gly Lys Asn Glu Leu Lys Thr Leu
65                  70                  75                  80

His Asp Leu Glu Trp Met Thr Gly Leu Thr Leu Leu Arg Gly Asp Ala
                85                  90                  95
```

```
Leu Met Cys Gly Phe Tyr Met Asn Glu Leu Leu Arg Leu Leu Pro
            100                 105                 110
Arg Asp Asp Ala His Thr Gln Leu Phe Glu Tyr Tyr Ala Gln Thr Ile
        115                 120                 125
Gln Leu Leu Ser Thr Leu Gln Gln Asp Ala Gly Ser Gly Gln Leu Ala
    130                 135                 140
Glu Ile Met Arg Arg Phe Glu Leu Lys Met Leu Gln Glu Leu Gly Tyr
145                 150                 155                 160
Ala Val Pro Leu Thr His Asp Glu His Gly Glu Val Ile His Ala Asp
                165                 170                 175
Glu Ile Tyr Arg Phe Glu Ala Asp Tyr Gly Ala Cys Ala Pro Ser Ala
            180                 185                 190
Thr Arg Asn Gly Leu Leu Val Gln Gly Ala Thr Leu Leu Glu Met Ala
        195                 200                 205
Arg Gly Asn Tyr Ser Ser Ala Thr Thr Gln Ser Gln Ser Lys Gln Leu
    210                 215                 220
Met Arg Tyr Leu Leu Gln His Tyr Leu Gly Glu Lys Pro Leu His Thr
225                 230                 235                 240
Arg Gln Leu Leu Val Asp Leu Gln Asp Phe
                245                 250

<210> SEQ ID NO 7
<211> LENGTH: 315
<212> TYPE: DNA
<213> ORGANISM: Methylophilus methylotrophus
<220> FEATURE:
<221> NAME/KEY: CDS
<222> LOCATION: (1)..(315)
<223> OTHER INFORMATION:

<400> SEQUENCE: 7 atg aca ctc aca aaa gct gac ttg gcc gat ttg ttg ttt gaa caa gtc      48
Met Thr Leu Thr Lys Ala Asp Leu Ala Asp Leu Leu Phe Glu Gln Val
1               5                   10                  15 ggg cta aac aag cgt gaa gcc aag gac atg gta gaa gcg ttt ttt gaa      96
Gly Leu Asn Lys Arg Glu Ala Lys Asp Met Val Glu Ala Phe Phe Glu
            20                  25                  30 gaa gtc cgt aat gca ctg gaa caa ggc gat agc gtt aaa ctg tct ggt     144
Glu Val Arg Asn Ala Leu Glu Gln Gly Asp Ser Val Lys Leu Ser Gly
        35                  40                  45 ttt ggt aat ttt gaa ttg cgt act aaa tcc gaa cgt cct ggc cgt aac     192
Phe Gly Asn Phe Glu Leu Arg Thr Lys Ser Glu Arg Pro Gly Arg Asn
    50                  55                  60 ccg aaa act ggc gaa gaa atc ccg atc tct gca cgt cgt gta gtg act     240
Pro Lys Thr Gly Glu Glu Ile Pro Ile Ser Ala Arg Arg Val Val Thr
65                  70                  75                  80 ttt cac gcc agt cag aaa tta aaa ttg cgc gta gaa gag cac tac gcc     288
Phe His Ala Ser Gln Lys Leu Lys Leu Arg Val Glu Glu His Tyr Ala
                85                  90                  95 gaa caa cct ttg caa gca caa gcc tga                                 315
Glu Gln Pro Leu Gln Ala Gln Ala
            100

<210> SEQ ID NO 8
<211> LENGTH: 104
<212> TYPE: PRT
<213> ORGANISM: Methylophilus methylotrophus

<400> SEQUENCE: 8
```

```
Met Thr Leu Thr Lys Ala Asp Leu Ala Asp Leu Leu Phe Glu Gln Val
1               5                  10                  15

Gly Leu Asn Lys Arg Glu Ala Lys Asp Met Val Glu Ala Phe Phe Glu
                20                  25                  30

Glu Val Arg Asn Ala Leu Glu Gln Gly Asp Ser Val Lys Leu Ser Gly
            35                  40                  45

Phe Gly Asn Phe Glu Leu Arg Thr Lys Ser Glu Arg Pro Gly Arg Asn
    50                  55                  60

Pro Lys Thr Gly Glu Glu Ile Pro Ile Ser Ala Arg Arg Val Val Thr
65              70                  75                  80

Phe His Ala Ser Gln Lys Leu Lys Leu Arg Val Glu Glu His Tyr Ala
                85                  90                  95

Glu Gln Pro Leu Gln Ala Gln Ala
                100
```

<210> SEQ ID NO 9
<211> LENGTH: 288
<212> TYPE: DNA
<213> ORGANISM: Methylophilus methylotrophus
<220> FEATURE:
<221> NAME/KEY: CDS
<222> LOCATION: (1)..(288)
<223> OTHER INFORMATION:

<400> SEQUENCE: 9

```
atg aca cga tct gaa ctg ata gac ctg ctt gcc cag cgc ttt ccg caa     48
Met Thr Arg Ser Glu Leu Ile Asp Leu Leu Ala Gln Arg Phe Pro Gln
1               5                  10                  15 tta gtg ctg aaa gat gcc gag tta tcc gtc aaa acc atc ctg gat gca     96
Leu Val Leu Lys Asp Ala Glu Leu Ser Val Lys Thr Ile Leu Asp Ala
                20                  25                  30 atg acg gaa aac ctg gcc aca ggc gag cgt atc gaa ata cgc ggt ttt    144
Met Thr Glu Asn Leu Ala Thr Gly Glu Arg Ile Glu Ile Arg Gly Phe
            35                  40                  45 ggc agc ttc agc ctc aat tac cgc ccg ccc cgt ttg gga cgt aac ccg    192
Gly Ser Phe Ser Leu Asn Tyr Arg Pro Pro Arg Leu Gly Arg Asn Pro
    50                  55                  60 aaa aca ggc act aag gtg caa gtt ccg gct aaa tat gtc cct cac ttt    240
Lys Thr Gly Thr Lys Val Gln Val Pro Ala Lys Tyr Val Pro His Phe
65              70                  75                  80 aag gct ggt aaa gag ctg cgt gac cgc gta gat gca atc gaa tct taa    288
Lys Ala Gly Lys Glu Leu Arg Asp Arg Val Asp Ala Ile Glu Ser
                85                  90                  95
```

<210> SEQ ID NO 10
<211> LENGTH: 95
<212> TYPE: PRT
<213> ORGANISM: Methylophilus methylotrophus

<400> SEQUENCE: 10

```
Met Thr Arg Ser Glu Leu Ile Asp Leu Leu Ala Gln Arg Phe Pro Gln
1               5                  10                  15

Leu Val Leu Lys Asp Ala Glu Leu Ser Val Lys Thr Ile Leu Asp Ala
                20                  25                  30

Met Thr Glu Asn Leu Ala Thr Gly Glu Arg Ile Glu Ile Arg Gly Phe
            35                  40                  45

Gly Ser Phe Ser Leu Asn Tyr Arg Pro Pro Arg Leu Gly Arg Asn Pro
    50                  55                  60

Lys Thr Gly Thr Lys Val Gln Val Pro Ala Lys Tyr Val Pro His Phe
65              70                  75                  80
```

<210> SEQ ID NO 11
<211> LENGTH: 1950
<212> TYPE: DNA
<213> ORGANISM: Methylophilus methylotrophus
<220> FEATURE:
<221> NAME/KEY: CDS
<222> LOCATION: (1)..(1950)
<223> OTHER INFORMATION:

<400> SEQUENCE: 11

| | | |
|---|---|---|
| atg gcc aga ccc aaa gca gat aaa agt tta gat aaa gaa ctc gga atc<br>Met Ala Arg Pro Lys Ala Asp Lys Ser Leu Asp Lys Glu Leu Gly Ile<br>1                          5                        10                    15 | | 48 |

Lys Ala Gly Lys Glu Leu Arg Asp Arg Val Asp Ala Ile Glu Ser
                        85                        90                    95

<210> SEQ ID NO 11
<211> LENGTH: 1950
<212> TYPE: DNA
<213> ORGANISM: Methylophilus methylotrophus
<220> FEATURE:
<221> NAME/KEY: CDS
<222> LOCATION: (1)..(1950)
<223> OTHER INFORMATION:

<400> SEQUENCE: 11

```
atg gcc aga ccc aaa gca gat aaa agt tta gat aaa gaa ctc gga atc        48
Met Ala Arg Pro Lys Ala Asp Lys Ser Leu Asp Lys Glu Leu Gly Ile
1               5                   10                  15 aac gaa gtc gaa acc cct aaa gat ccc gct acc cag gca ctg gat gcc        96
Asn Glu Val Glu Thr Pro Lys Asp Pro Ala Thr Gln Ala Leu Asp Ala
            20                  25                  30 gag gca cgc cgt acc cgc ctg aaa acc ctg att gtc ctg ggt aaa gag      144
Glu Ala Arg Arg Thr Arg Leu Lys Thr Leu Ile Val Leu Gly Lys Glu
        35                  40                  45 cgt ggc tac ctg acc tac gcc gaa atc aat gac cac ctg ccg gac gat      192
Arg Gly Tyr Leu Thr Tyr Ala Glu Ile Asn Asp His Leu Pro Asp Asp
    50                  55                  60 gtg caa gac tcc gag cag atc gag agc att atc ggc atg atc aat gac      240
Val Gln Asp Ser Glu Gln Ile Glu Ser Ile Ile Gly Met Ile Asn Asp
65                  70                  75                  80 atg ggt atc cag gtc tat gaa gaa gcg ccg gat gcc gaa gtg ttg ttg      288
Met Gly Ile Gln Val Tyr Glu Glu Ala Pro Asp Ala Glu Val Leu Leu
                85                  90                  95 atg tct gat gcg cca cca gct gtg act gat gat gat gcg gca gaa gag      336
Met Ser Asp Ala Pro Pro Ala Val Thr Asp Asp Asp Ala Ala Glu Glu
            100                 105                 110 gct gag cag gcc ttg gca acc gtg gac tct gaa ttt ggt cgc acg act      384
Ala Glu Gln Ala Leu Ala Thr Val Asp Ser Glu Phe Gly Arg Thr Thr
        115                 120                 125 gac cca gta cgt atg tac atg cgc gaa atg ggg act gtt gac ctg ttg      432
Asp Pro Val Arg Met Tyr Met Arg Glu Met Gly Thr Val Asp Leu Leu
    130                 135                 140 acg cgt gag ggc gaa atc gag atc gcc aaa cgc att gag gat ggc ctc      480
Thr Arg Glu Gly Glu Ile Glu Ile Ala Lys Arg Ile Glu Asp Gly Leu
145                 150                 155                 160 aag cac atg gtg cag gcg att gca gcc tgt cca acg acc atc gcc cag      528
Lys His Met Val Gln Ala Ile Ala Ala Cys Pro Thr Thr Ile Ala Gln
                165                 170                 175 ttg ctg gag atg gtc gac aag gtt gaa aaa gac gaa atg agc gtt gat      576
Leu Leu Glu Met Val Asp Lys Val Glu Lys Asp Glu Met Ser Val Asp
            180                 185                 190 gaa ctg gta gac ggt ttg atc gat agt gat ttg ggt ctg gat gac gcg      624
Glu Leu Val Asp Gly Leu Ile Asp Ser Asp Leu Gly Leu Asp Asp Ala
        195                 200                 205 ctg gcg gcc gca gat gtt gag gaa gaa gaa gcc gac gac gaa gaa gat      672
Leu Ala Ala Ala Asp Val Glu Glu Glu Glu Ala Asp Asp Glu Glu Asp
    210                 215                 220 gaa gat gat gaa gaa gat ggt gat gcc aaa gcg tct gcc atg tct gcc      720
Glu Asp Asp Glu Glu Asp Gly Asp Ala Lys Ala Ser Ala Met Ser Ala
225                 230                 235                 240 gaa gcg ctg gcc aaa ctc aag gat gaa gtc ttg tca cgc ttt gcc gtc      768
Glu Ala Leu Ala Lys Leu Lys Asp Glu Val Leu Ser Arg Phe Ala Val
                245                 250                 255
```

| | |
|---|---:|
| atc cgt gct gcc aac gca aaa atg aac acc atc cgt gag gat aaa ggc<br>Ile Arg Ala Ala Asn Ala Lys Met Asn Thr Ile Arg Glu Asp Lys Gly<br>260 265 270 | 816 |
| acc agc gat gca gaa tat aaa act ttg cat cag caa gta ctg gat gag<br>Thr Ser Asp Ala Glu Tyr Lys Thr Leu His Gln Gln Val Leu Asp Glu<br>275 280 285 | 864 |
| ctg acc gcc ttc cgt ttc tct gcc aaa cag gtt gag gcc ttg tgc gac<br>Leu Thr Ala Phe Arg Phe Ser Ala Lys Gln Val Glu Ala Leu Cys Asp<br>290 295 300 | 912 |
| cag gtg cgt aac atg gtg gaa gag gtg cgt acg cac gaa cgc aag atc<br>Gln Val Arg Asn Met Val Glu Glu Val Arg Thr His Glu Arg Lys Ile<br>305 310 315 320 | 960 |
| atg gag ttt tgt gta gac aag gcc aat atg ccg cgt cag caa ttc atc<br>Met Glu Phe Cys Val Asp Lys Ala Asn Met Pro Arg Gln Gln Phe Ile<br>325 330 335 | 1008 |
| aag agc ttt gtc ggt aac gaa atc aac ctt aac tgg ctc gat gac gag<br>Lys Ser Phe Val Gly Asn Glu Ile Asn Leu Asn Trp Leu Asp Asp Glu<br>340 345 350 | 1056 |
| ctg gca ggc aaa cct gcc tat ggt gag cgt tta gaa cgt ttc agg cac<br>Leu Ala Gly Lys Pro Ala Tyr Gly Glu Arg Leu Glu Arg Phe Arg His<br>355 360 365 | 1104 |
| tct atc cta gac cag caa gag cgt tta caa aac ctg cag aac cgc gtg<br>Ser Ile Leu Asp Gln Gln Glu Arg Leu Gln Asn Leu Gln Asn Arg Val<br>370 375 380 | 1152 |
| gga ttg cca atc aaa gag ctg cgt gaa atc aac aag caa atg acc act<br>Gly Leu Pro Ile Lys Glu Leu Arg Glu Ile Asn Lys Gln Met Thr Thr<br>385 390 395 400 | 1200 |
| ggc gaa gct cgt gca cga cgc gcc aag cgc gaa atg atc gag gcc aac<br>Gly Glu Ala Arg Ala Arg Arg Ala Lys Arg Glu Met Ile Glu Ala Asn<br>405 410 415 | 1248 |
| ctg cgt ctg gtg atc tcc att gca aaa aaa tac acc aat cgt ggt ttg<br>Leu Arg Leu Val Ile Ser Ile Ala Lys Lys Tyr Thr Asn Arg Gly Leu<br>420 425 430 | 1296 |
| cag ttc ctc gac ttg atc caa gag ggc aac atc ggc ttg atg aaa gcc<br>Gln Phe Leu Asp Leu Ile Gln Glu Gly Asn Ile Gly Leu Met Lys Ala<br>435 440 445 | 1344 |
| gtg gat aag ttt gaa tac cgc cgt ggt tac aaa ttt tct acc tat gcg<br>Val Asp Lys Phe Glu Tyr Arg Arg Gly Tyr Lys Phe Ser Thr Tyr Ala<br>450 455 460 | 1392 |
| aca tgg tgg att cgc cag gcg att acc cgt tca atc gca gac cag gca<br>Thr Trp Trp Ile Arg Gln Ala Ile Thr Arg Ser Ile Ala Asp Gln Ala<br>465 470 475 480 | 1440 |
| cgt acc atc cgt atc ccg gtc cac atg atc gaa acc atc aac aag atg<br>Arg Thr Ile Arg Ile Pro Val His Met Ile Glu Thr Ile Asn Lys Met<br>485 490 495 | 1488 |
| aac cgt atc agc cgc cag atc ttg caa gaa act ggc ctg gaa cct gat<br>Asn Arg Ile Ser Arg Gln Ile Leu Gln Glu Thr Gly Leu Glu Pro Asp<br>500 505 510 | 1536 |
| ccg gct act ctg gct gaa aaa atg gat atg ccg gaa gaa aaa atc cgc<br>Pro Ala Thr Leu Ala Glu Lys Met Asp Met Pro Glu Glu Lys Ile Arg<br>515 520 525 | 1584 |
| aaa atc ctc aaa atc agc aaa gag ccg atc tca atg gaa acg ccg att<br>Lys Ile Leu Lys Ile Ser Lys Glu Pro Ile Ser Met Glu Thr Pro Ile<br>530 535 540 | 1632 |
| ggt gac gat gaa gac agc cac ttg ggc gac ttt att gaa gac aac acc<br>Gly Asp Asp Glu Asp Ser His Leu Gly Asp Phe Ile Glu Asp Asn Thr<br>545 550 555 560 | 1680 |
| aca ctg gca ccg atg gac gca gct gtt tac gcc agc ctg cgt gac gcc<br>Thr Leu Ala Pro Met Asp Ala Ala Val Tyr Ala Ser Leu Arg Asp Ala | 1728 |

-continued

```
                        565                 570                 575
acc agt gaa gtg ctg gaa tca ctg acc cca cgt gaa gcc aaa gtg ctg      1776
Thr Ser Glu Val Leu Glu Ser Leu Thr Pro Arg Glu Ala Lys Val Leu
            580                 585                 590 cgc atg cgc ttt ggt atc gaa atg aac acc gac cac acg ctg gaa gaa      1824
Arg Met Arg Phe Gly Ile Glu Met Asn Thr Asp His Thr Leu Glu Glu
            595                 600                 605 gtt ggc aaa caa ttt gac gtc acc cgt gaa cgt atc cgc cag att gaa      1872
Val Gly Lys Gln Phe Asp Val Thr Arg Glu Arg Ile Arg Gln Ile Glu
            610                 615                 620 gct aag gcc ctg cgt aaa ctg cgt cac ccg acc cgc tcg gaa cgc ctg      1920
Ala Lys Ala Leu Arg Lys Leu Arg His Pro Thr Arg Ser Glu Arg Leu
625                 630                 635                 640 cgc agc ttc tta gaa aac ggt cag gat tag                              1950
Arg Ser Phe Leu Glu Asn Gly Gln Asp
                645
```

<210> SEQ ID NO 12
<211> LENGTH: 649
<212> TYPE: PRT
<213> ORGANISM: Methylophilus methylotrophus

<400> SEQUENCE: 12

```
Met Ala Arg Pro Lys Ala Asp Lys Ser Leu Asp Lys Glu Leu Gly Ile
1               5                   10                  15

Asn Glu Val Glu Thr Pro Lys Asp Pro Ala Thr Gln Ala Leu Asp Ala
                20                  25                  30

Glu Ala Arg Arg Thr Arg Leu Lys Thr Leu Ile Val Leu Gly Lys Glu
            35                  40                  45

Arg Gly Tyr Leu Thr Tyr Ala Glu Ile Asn Asp His Leu Pro Asp Asp
        50                  55                  60

Val Gln Asp Ser Glu Gln Ile Glu Ser Ile Gly Met Ile Asn Asp
65                  70                  75                  80

Met Gly Ile Gln Val Tyr Glu Glu Ala Pro Asp Ala Glu Val Leu Leu
                85                  90                  95

Met Ser Asp Ala Pro Pro Ala Val Thr Asp Asp Ala Ala Glu Glu
            100                 105                 110

Ala Glu Gln Ala Leu Ala Thr Val Asp Ser Glu Phe Gly Arg Thr Thr
        115                 120                 125

Asp Pro Val Arg Met Tyr Met Arg Glu Met Gly Thr Val Asp Leu Leu
130                 135                 140

Thr Arg Glu Gly Glu Ile Glu Ile Ala Lys Arg Ile Glu Asp Gly Leu
145                 150                 155                 160

Lys His Met Val Gln Ala Ile Ala Ala Cys Pro Thr Thr Ile Ala Gln
                165                 170                 175

Leu Leu Glu Met Val Asp Lys Val Glu Lys Asp Glu Met Ser Val Asp
            180                 185                 190

Glu Leu Val Asp Gly Leu Ile Asp Ser Asp Leu Gly Leu Asp Asp Ala
        195                 200                 205

Leu Ala Ala Asp Val Glu Glu Glu Ala Asp Asp Glu Glu Asp
    210                 215                 220

Glu Asp Asp Glu Glu Asp Gly Asp Ala Lys Ala Ser Ala Met Ser Ala
225                 230                 235                 240

Glu Ala Leu Ala Lys Leu Lys Asp Glu Val Leu Ser Arg Phe Ala Val
                245                 250                 255

Ile Arg Ala Ala Asn Ala Lys Met Asn Thr Ile Arg Glu Asp Lys Gly
```

```
                   260                 265                 270
Thr Ser Asp Ala Glu Tyr Lys Thr Leu His Gln Gln Val Leu Asp Glu
        275                 280                 285

Leu Thr Ala Phe Arg Phe Ser Ala Lys Gln Val Glu Ala Leu Cys Asp
    290                 295                 300

Gln Val Arg Asn Met Val Glu Val Arg Thr His Glu Arg Lys Ile
305                 310                 315                 320

Met Glu Phe Cys Val Asp Lys Ala Asn Met Pro Arg Gln Gln Phe Ile
                325                 330                 335

Lys Ser Phe Val Gly Asn Glu Ile Asn Leu Asn Trp Leu Asp Asp Glu
            340                 345                 350

Leu Ala Gly Lys Pro Ala Tyr Gly Glu Arg Leu Glu Arg Phe Arg His
        355                 360                 365

Ser Ile Leu Asp Gln Gln Arg Leu Gln Asn Leu Gln Asn Arg Val
    370                 375                 380

Gly Leu Pro Ile Lys Glu Leu Arg Glu Ile Asn Lys Gln Met Thr Thr
385                 390                 395                 400

Gly Glu Ala Arg Ala Arg Arg Ala Lys Arg Glu Met Ile Glu Ala Asn
                405                 410                 415

Leu Arg Leu Val Ile Ser Ile Ala Lys Lys Tyr Thr Asn Arg Gly Leu
            420                 425                 430

Gln Phe Leu Asp Leu Ile Gln Glu Gly Asn Ile Gly Leu Met Lys Ala
        435                 440                 445

Val Asp Lys Phe Glu Tyr Arg Arg Gly Tyr Lys Phe Ser Thr Tyr Ala
    450                 455                 460

Thr Trp Trp Ile Arg Gln Ala Ile Thr Arg Ser Ile Ala Asp Gln Ala
465                 470                 475                 480

Arg Thr Ile Arg Ile Pro Val His Met Ile Glu Thr Ile Asn Lys Met
                485                 490                 495

Asn Arg Ile Ser Arg Gln Ile Leu Gln Glu Thr Gly Leu Glu Pro Asp
            500                 505                 510

Pro Ala Thr Leu Ala Glu Lys Met Asp Met Pro Glu Glu Lys Ile Arg
        515                 520                 525

Lys Ile Leu Lys Ile Ser Lys Glu Pro Ile Ser Met Glu Thr Pro Ile
    530                 535                 540

Gly Asp Asp Glu Asp Ser His Leu Gly Asp Phe Ile Glu Asp Asn Thr
545                 550                 555                 560

Thr Leu Ala Pro Met Asp Ala Ala Val Tyr Ala Ser Leu Arg Asp Ala
                565                 570                 575

Thr Ser Glu Val Leu Glu Ser Leu Thr Pro Arg Glu Ala Lys Val Leu
            580                 585                 590

Arg Met Arg Phe Gly Ile Glu Met Asn Thr Asp His Thr Leu Glu Glu
        595                 600                 605

Val Gly Lys Gln Phe Asp Val Thr Arg Glu Arg Ile Arg Gln Ile Glu
    610                 615                 620

Ala Lys Ala Leu Arg Lys Leu Arg His Pro Thr Arg Ser Glu Arg Leu
625                 630                 635                 640

Arg Ser Phe Leu Glu Asn Gly Gln Asp
                645

<210> SEQ ID NO 13
<211> LENGTH: 741
<212> TYPE: DNA
<213> ORGANISM: Methylophilus methylotrophus
```

<220> FEATURE:
<221> NAME/KEY: CDS
<222> LOCATION: (1)..(741)
<223> OTHER INFORMATION:

<400> SEQUENCE: 13

```
atg tta cac aca gca aat tta gaa gcg tta aca cgc acc ggg ttc gtc        48
Met Leu His Thr Ala Asn Leu Glu Ala Leu Thr Arg Thr Gly Phe Val
1               5                   10                  15 gaa aat aac aca aaa gcg tat act act ccc aat cat aaa att acc caa        96
Glu Asn Asn Thr Lys Ala Tyr Thr Thr Pro Asn His Lys Ile Thr Gln
            20                  25                  30 ggg agt cat cgc gat atg act gtt cag gcg gca agc gcc aaa cag caa       144
Gly Ser His Arg Asp Met Thr Val Gln Ala Ala Ser Ala Lys Gln Gln
        35                  40                  45 gag aac aaa gag ttt gac cag atg ctg gtc gag cgt gct cag cag ggc       192
Glu Asn Lys Glu Phe Asp Gln Met Leu Val Glu Arg Ala Gln Gln Gly
    50                  55                  60 gac aag cgt gcc ttt gga ttg ttg gtg gaa aaa tat cac cgt aag ctt       240
Asp Lys Arg Ala Phe Gly Leu Leu Val Glu Lys Tyr His Arg Lys Leu
65                  70                  75                  80 gga cgc ctt tta tcg cgc atg att cgc gat cag gcg gaa gtg gaa gat       288
Gly Arg Leu Leu Ser Arg Met Ile Arg Asp Gln Ala Glu Val Glu Asp
                85                  90                  95 gtg gtg cag gag tct ttt atc aag gct tat cgc gcg ttg cac agc ttc       336
Val Val Gln Glu Ser Phe Ile Lys Ala Tyr Arg Ala Leu His Ser Phe
            100                 105                 110 cgt ggc gac agt gca ttt tat aca tgg ttg tat cgt att ggc att aat       384
Arg Gly Asp Ser Ala Phe Tyr Thr Trp Leu Tyr Arg Ile Gly Ile Asn
        115                 120                 125 act gcc aaa aac tac ctg gtc tcc atg ggc cgc aag cca caa gtg ctg       432
Thr Ala Lys Asn Tyr Leu Val Ser Met Gly Arg Lys Pro Gln Val Leu
    130                 135                 140 caa gac gtg gaa atc gaa gat gta gaa aac ttc gat gaa ggc gat gat       480
Gln Asp Val Glu Ile Glu Asp Val Glu Asn Phe Asp Glu Gly Asp Asp
145                 150                 155                 160 atg cgc aca ctg gag acc cca gaa acg tcc ctg atg acg aaa gag att       528
Met Arg Thr Leu Glu Thr Pro Glu Thr Ser Leu Met Thr Lys Glu Ile
                165                 170                 175 gcg caa acg gtc aat gat gcg att gcg gcg ttg cct gaa gag ttg cgt       576
Ala Gln Thr Val Asn Asp Ala Ile Ala Ala Leu Pro Glu Glu Leu Arg
            180                 185                 190 act gca att aca ttg cgc gag ctt gaa gga ttg agt tat gaa gac att       624
Thr Ala Ile Thr Leu Arg Glu Leu Glu Gly Leu Ser Tyr Glu Asp Ile
        195                 200                 205 gct aac gtg atg caa tgt ccg atc ggg act gtg cgt tca cgt att ttc       672
Ala Asn Val Met Gln Cys Pro Ile Gly Thr Val Arg Ser Arg Ile Phe
    210                 215                 220 cgg gcg cgt gaa acg att gcg acc aaa ttg aga ccg ttg ttg gat acg       720
Arg Ala Arg Glu Thr Ile Ala Thr Lys Leu Arg Pro Leu Leu Asp Thr
225                 230                 235                 240 cca cag cac aag cgc tgg tag                                           741
Pro Gln His Lys Arg Trp
                245
```

<210> SEQ ID NO 14
<211> LENGTH: 246
<212> TYPE: PRT
<213> ORGANISM: Methylophilus methylotrophus

<400> SEQUENCE: 14

```
Met Leu His Thr Ala Asn Leu Glu Ala Leu Thr Arg Thr Gly Phe Val
 1               5                  10                  15

Glu Asn Asn Thr Lys Ala Tyr Thr Thr Pro Asn His Lys Ile Thr Gln
             20                  25                  30

Gly Ser His Arg Asp Met Thr Val Gln Ala Ala Ser Ala Lys Gln Gln
         35                  40                  45

Glu Asn Lys Glu Phe Asp Gln Met Leu Val Glu Arg Ala Gln Gln Gly
     50                  55                  60

Asp Lys Arg Ala Phe Gly Leu Leu Val Glu Lys Tyr His Arg Lys Leu
65                  70                  75                  80

Gly Arg Leu Leu Ser Arg Met Ile Arg Asp Gln Ala Glu Val Glu Asp
                 85                  90                  95

Val Val Gln Glu Ser Phe Ile Lys Ala Tyr Arg Ala Leu His Ser Phe
                100                 105                 110

Arg Gly Asp Ser Ala Phe Tyr Thr Trp Leu Tyr Arg Ile Gly Ile Asn
            115                 120                 125

Thr Ala Lys Asn Tyr Leu Val Ser Met Gly Arg Lys Pro Gln Val Leu
        130                 135                 140

Gln Asp Val Glu Ile Glu Asp Val Glu Asn Phe Asp Glu Gly Asp Asp
145                 150                 155                 160

Met Arg Thr Leu Glu Thr Pro Glu Thr Ser Leu Met Thr Lys Glu Ile
                165                 170                 175

Ala Gln Thr Val Asn Asp Ala Ile Ala Ala Leu Pro Glu Glu Leu Arg
            180                 185                 190

Thr Ala Ile Thr Leu Arg Glu Leu Glu Gly Leu Ser Tyr Glu Asp Ile
        195                 200                 205

Ala Asn Val Met Gln Cys Pro Ile Gly Thr Val Arg Ser Arg Ile Phe
    210                 215                 220

Arg Ala Arg Glu Thr Ile Ala Thr Lys Leu Arg Pro Leu Leu Asp Thr
225                 230                 235                 240

Pro Gln His Lys Arg Trp
                245

<210> SEQ ID NO 15
<211> LENGTH: 777
<212> TYPE: DNA
<213> ORGANISM: Methylophilus methylotrophus
<220> FEATURE:
<221> NAME/KEY: CDS
<222> LOCATION: (1)..(777)
<223> OTHER INFORMATION:

<400> SEQUENCE: 15 gtg ctc acg gca gag gaa gag tat ggt tac gct acc cgc ctg aaa gaa      48
Val Leu Thr Ala Glu Glu Glu Tyr Gly Tyr Ala Thr Arg Leu Lys Glu
 1               5                  10                  15 agc ggt gac ctg gaa tct gcg cgc gca ctg att gtg tcg cat ttg cgt      96
Ser Gly Asp Leu Glu Ser Ala Arg Ala Leu Ile Val Ser His Leu Arg
             20                  25                  30 ctg gtc gcc agt att gcg cgt ggt tac agc ggt tat ggc ttg cca cag     144
Leu Val Ala Ser Ile Ala Arg Gly Tyr Ser Gly Tyr Gly Leu Pro Gln
         35                  40                  45 tcc gac ctg att cag gaa ggc aat att ggc ctg atg aaa gcg gtt aaa     192
Ser Asp Leu Ile Gln Glu Gly Asn Ile Gly Leu Met Lys Ala Val Lys
     50                  55                  60 cgc ttt gac ccg gat cgt ggc gtg cgc ctg gtt tca ttt gcc atg cac     240
Arg Phe Asp Pro Asp Arg Gly Val Arg Leu Val Ser Phe Ala Met His
65                  70                  75                  80
```

```
tgg atc aaa gcc gag att cac gaa tac att gtg cgc aac tgg cgc ctg        288
Trp Ile Lys Ala Glu Ile His Glu Tyr Ile Val Arg Asn Trp Arg Leu
             85                  90                  95 gtg aaa aca gcc acg acc aag gca cag cgc aaa ctg ttc ttc aac ctg        336
Val Lys Thr Ala Thr Thr Lys Ala Gln Arg Lys Leu Phe Phe Asn Leu
            100                 105                 110 cgt agc atg aag caa ggg ttt gaa acc ttg agc cag gat gat gtg cat        384
Arg Ser Met Lys Gln Gly Phe Glu Thr Leu Ser Gln Asp Asp Val His
        115                 120                 125 cgc atc gcg acc gag ctc aat gtg aaa ccg gaa gaa gtg act gaa atg        432
Arg Ile Ala Thr Glu Leu Asn Val Lys Pro Glu Glu Val Thr Glu Met
    130                 135                 140 gaa tat cgc ctc aat ggt cag gag att tca ctg gat gcg cag gta gat        480
Glu Tyr Arg Leu Asn Gly Gln Glu Ile Ser Leu Asp Ala Gln Val Asp
145                 150                 155                 160 gaa gat ggc gaa gaa gta tat agc cct att tcc ttc ctg gag gat gaa        528
Glu Asp Gly Glu Glu Val Tyr Ser Pro Ile Ser Phe Leu Glu Asp Glu
                165                 170                 175 ggc cct gag cct tct acg ctg ctg gaa aat ctg cag aat gag cac atg        576
Gly Pro Glu Pro Ser Thr Leu Leu Glu Asn Leu Gln Asn Glu His Met
            180                 185                 190 cag act gaa ggc tta agc aac gca ttg cag caa ctt gat gag cgt agc        624
Gln Thr Glu Gly Leu Ser Asn Ala Leu Gln Gln Leu Asp Glu Arg Ser
        195                 200                 205 cgc cgc gta ttg cag gca cgc tgg ctg acc gaa ggt gat tca gcc acc        672
Arg Arg Val Leu Gln Ala Arg Trp Leu Thr Glu Gly Asp Ser Ala Thr
    210                 215                 220 ttg cat gag ctg gct gca gaa ttc aat gtg tcg gct gag cgt atc cgc        720
Leu His Glu Leu Ala Ala Glu Phe Asn Val Ser Ala Glu Arg Ile Arg
225                 230                 235                 240 cag att gag caa aaa gcg atg caa aaa att aaa acc tat atg ctg gaa        768
Gln Ile Glu Gln Lys Ala Met Gln Lys Ile Lys Thr Tyr Met Leu Glu
                245                 250                 255 agc aaa taa                                                            777
Ser Lys <210> SEQ ID NO 16
<211> LENGTH: 258
<212> TYPE: PRT
<213> ORGANISM: Methylophilus methylotrophus

<400> SEQUENCE: 16

Val Leu Thr Ala Glu Glu Tyr Gly Tyr Ala Thr Arg Leu Lys Glu
1               5                   10                  15

Ser Gly Asp Leu Glu Ser Ala Arg Ala Leu Ile Val Ser His Leu Arg
            20                  25                  30

Leu Val Ala Ser Ile Ala Arg Gly Tyr Ser Gly Tyr Gly Leu Pro Gln
        35                  40                  45

Ser Asp Leu Ile Gln Glu Gly Asn Ile Gly Leu Met Lys Ala Val Lys
    50                  55                  60

Arg Phe Asp Pro Asp Arg Gly Val Arg Leu Val Ser Phe Ala Met His
65                  70                  75                  80

Trp Ile Lys Ala Glu Ile His Glu Tyr Ile Val Arg Asn Trp Arg Leu
                85                  90                  95

Val Lys Thr Ala Thr Thr Lys Ala Gln Arg Lys Leu Phe Phe Asn Leu
            100                 105                 110

Arg Ser Met Lys Gln Gly Phe Glu Thr Leu Ser Gln Asp Asp Val His
        115                 120                 125
```

```
Arg Ile Ala Thr Glu Leu Asn Val Lys Pro Glu Val Thr Glu Met
        130                 135                 140

Glu Tyr Arg Leu Asn Gly Gln Glu Ile Ser Leu Asp Ala Gln Val Asp
145                 150                 155                 160

Glu Asp Gly Glu Val Tyr Ser Pro Ile Ser Phe Leu Glu Asp Glu
                165                 170                 175

Gly Pro Glu Pro Ser Thr Leu Leu Glu Asn Leu Gln Asn Glu His Met
            180                 185                 190

Gln Thr Glu Gly Leu Ser Asn Ala Leu Gln Gln Leu Asp Glu Arg Ser
        195                 200                 205

Arg Arg Val Leu Gln Ala Arg Trp Leu Thr Glu Gly Asp Ser Ala Thr
210                 215                 220

Leu His Glu Leu Ala Ala Glu Phe Asn Val Ser Ala Glu Arg Ile Arg
225                 230                 235                 240

Gln Ile Glu Gln Lys Ala Met Gln Lys Ile Lys Thr Tyr Met Leu Glu
                245                 250                 255

Ser Lys
```

<210> SEQ ID NO 17
<211> LENGTH: 1551
<212> TYPE: DNA
<213> ORGANISM: Methylophilus methylotrophus
<220> FEATURE:
<221> NAME/KEY: CDS
<222> LOCATION: (1)..(1551)
<223> OTHER INFORMATION:

<400> SEQUENCE: 17

```
atg aag caa aac ctg caa tta cgc att tca caa aac ctg gca ctg act      48
Met Lys Gln Asn Leu Gln Leu Arg Ile Ser Gln Asn Leu Ala Leu Thr
1               5                   10                  15 ccg cag cta caa cag tct atc cgt ctg tta cag tta tcc aca ttg gag      96
Pro Gln Leu Gln Gln Ser Ile Arg Leu Leu Gln Leu Ser Thr Leu Glu
            20                  25                  30 ctc agc cag gag ctg gaa acc att ctt cag gaa aac ccg ttg ctg gag     144
Leu Ser Gln Glu Leu Glu Thr Ile Leu Gln Glu Asn Pro Leu Leu Glu
        35                  40                  45 atg gcc gat gga gaa gaa ggc gag ttt gag gac aat tca gca acc cct     192
Met Ala Asp Gly Glu Glu Gly Glu Phe Glu Asp Asn Ser Ala Thr Pro
    50                  55                  60 acc gaa act ata gaa tca gtc cat gca gac gat gcc aac tcg ttt gac     240
Thr Glu Thr Ile Glu Ser Val His Ala Asp Asp Ala Asn Ser Phe Asp
65                  70                  75                  80 ctg gcc acc cag caa gaa att act gca cct gcc gag acg ctg cgc gaa     288
Leu Ala Thr Gln Gln Glu Ile Thr Ala Pro Ala Glu Thr Leu Arg Glu
                85                  90                  95 gac tta cat gat gaa ctt ggc agc aat gaa ggc gaa ctg gct aat ctt     336
Asp Leu His Asp Glu Leu Gly Ser Asn Glu Gly Glu Leu Ala Asn Leu
            100                 105                 110 agc gaa gaa ttc aat cct ccc gaa ttt gaa gat aat tac gag gag ttt     384
Ser Glu Glu Phe Asn Pro Pro Glu Phe Glu Asp Asn Tyr Glu Glu Phe
        115                 120                 125 ggc agc acc agc aac tgg gat gag gca ggc cgc aac aac ctt gat gat     432
Gly Ser Thr Ser Asn Trp Asp Glu Ala Gly Arg Asn Asn Leu Asp Asp
    130                 135                 140 gag gat agt gat ttt tcg cgt cag gat gcc agc aat atc agc ctg cgc     480
Glu Asp Ser Asp Phe Ser Arg Gln Asp Ala Ser Asn Ile Ser Leu Arg
145                 150                 155                 160
```

```
gag cac ttg ctg gat cag att caa ctg gcg cat ttg tca cag cgg gac        528
Glu His Leu Leu Asp Gln Ile Gln Leu Ala His Leu Ser Gln Arg Asp
            165                 170                 175 atg acg ctg gtc aag tta ctc ctc gac agc att aat gac gac ggc tac        576
Met Thr Leu Val Lys Leu Leu Leu Asp Ser Ile Asn Asp Asp Gly Tyr
        180                 185                 190 ctt gag caa gac ttg cag gaa att gtt gaa cac ctg ccg att gag ctc        624
Leu Glu Gln Asp Leu Gln Glu Ile Val Glu His Leu Pro Ile Glu Leu
    195                 200                 205 gaa gtc gag ctg cta gaa ctt gag acc gca ctc aaa ctg ata cag aat        672
Glu Val Glu Leu Leu Glu Leu Glu Thr Ala Leu Lys Leu Ile Gln Asn
210                 215                 220 ctt gat ccg gta ggt gtc ggc gcc cgt gac ttg cgg gaa tgc ctg tta        720
Leu Asp Pro Val Gly Val Gly Ala Arg Asp Leu Arg Glu Cys Leu Leu
225                 230                 235                 240 ttg caa ctg caa cac ttg ccg gca gag acg cct tat tta cgt acg gcc        768
Leu Gln Leu Gln His Leu Pro Ala Glu Thr Pro Tyr Leu Arg Thr Ala
                245                 250                 255 atg gca ctc gca aaa gat cac ttg gcc ctc ctg gcc aac aaa gac ttt        816
Met Ala Leu Ala Lys Asp His Leu Ala Leu Leu Ala Asn Lys Asp Phe
            260                 265                 270 gtc aaa ctg cgc aaa ctg ctc agt tgc gat gaa acc gca ctt aaa ggt        864
Val Lys Leu Arg Lys Leu Leu Ser Cys Asp Glu Thr Ala Leu Lys Gly
        275                 280                 285 gcg caa caa ctg ata cgc cag caa aac ccc aaa cct ggc agc gaa ttt        912
Ala Gln Gln Leu Ile Arg Gln Gln Asn Pro Lys Pro Gly Ser Glu Phe
    290                 295                 300 gcc acc ttt agt cac gac cac ttt atc cag cat gat gtg gtg gtc aaa        960
Ala Thr Phe Ser His Asp His Phe Ile Gln His Asp Val Val Val Lys
305                 310                 315                 320 aaa atc aaa ggt atc tgg gtc gca tcg ctc aac gat ggc gtg att ccc       1008
Lys Ile Lys Gly Ile Trp Val Ala Ser Leu Asn Asp Gly Val Ile Pro
                325                 330                 335 aaa ctg cgg atc aac cag ctg tat gct gac atc ctc aaa cgc aac cgc       1056
Lys Leu Arg Ile Asn Gln Leu Tyr Ala Asp Ile Leu Lys Arg Asn Arg
            340                 345                 350 gaa agc tca ggc cag tat ctg caa agc cag atg cag gaa gcg aaa tgg       1104
Glu Ser Ser Gly Gln Tyr Leu Gln Ser Gln Met Gln Glu Ala Lys Trp
        355                 360                 365 atg atc aaa aat atc cag cag cgc ttc tcc acc att ctg cgc gtg tcg       1152
Met Ile Lys Asn Ile Gln Gln Arg Phe Ser Thr Ile Leu Arg Val Ser
    370                 375                 380 caa gcg att gta gac cgt cag cgc aat ttc ttt gag cat ggc gac att       1200
Gln Ala Ile Val Asp Arg Gln Arg Asn Phe Phe Glu His Gly Asp Ile
385                 390                 395                 400 gcc atg cgg cca ttg gtg ctt cgt gaa att gcc gaa gag cta gat ttg       1248
Ala Met Arg Pro Leu Val Leu Arg Glu Ile Ala Glu Glu Leu Asp Leu
                405                 410                 415 cat gaa agt act gtt tca cgg gtc acc acg cat aaa tat atg ctc aca       1296
His Glu Ser Thr Val Ser Arg Val Thr Thr His Lys Tyr Met Leu Thr
            420                 425                 430 cca cgt ggc gtt tac gag ctc aaa tat ttc ttt ggc agt tcg gtg gcg       1344
Pro Arg Gly Val Tyr Glu Leu Lys Tyr Phe Phe Gly Ser Ser Val Ala
        435                 440                 445 act gat gcg ggg ggc tct tgc tca gcg acg gcc atc cgc gcc ttg atc       1392
Thr Asp Ala Gly Gly Ser Cys Ser Ala Thr Ala Ile Arg Ala Leu Ile
    450                 455                 460 aag caa atg gtg gcc gaa gaa aat ccg aaa aaa ccg ctt tcg gat aac       1440
Lys Gln Met Val Ala Glu Glu Asn Pro Lys Lys Pro Leu Ser Asp Asn
465                 470                 475                 480
```

```
cag atc aca gat aca ttg gct caa caa ggc att gtg gtc gcg cgc cgc      1488
Gln Ile Thr Asp Thr Leu Ala Gln Gln Gly Ile Val Val Ala Arg Arg
            485                 490                 495 acc att gcc aaa tac cgt gag tct tta aat att ccg ccc gcc aat tta      1536
Thr Ile Ala Lys Tyr Arg Glu Ser Leu Asn Ile Pro Pro Ala Asn Leu
        500                 505                 510 cgc aaa tcg ctt taa                                                  1551
Arg Lys Ser Leu
        515
```

<210> SEQ ID NO 18
<211> LENGTH: 516
<212> TYPE: PRT
<213> ORGANISM: Methylophilus methylotrophus

<400> SEQUENCE: 18

```
Met Lys Gln Asn Leu Gln Leu Arg Ile Ser Gln Asn Leu Ala Leu Thr
1               5                   10                  15

Pro Gln Leu Gln Gln Ser Ile Arg Leu Leu Gln Leu Ser Thr Leu Glu
            20                  25                  30

Leu Ser Gln Glu Leu Glu Thr Ile Leu Gln Glu Asn Pro Leu Leu Glu
        35                  40                  45

Met Ala Asp Gly Glu Glu Gly Glu Phe Glu Asp Asn Ser Ala Thr Pro
    50                  55                  60

Thr Glu Thr Ile Glu Ser Val His Ala Asp Ala Asn Ser Phe Asp
65              70                  75                  80

Leu Ala Thr Gln Gln Glu Ile Thr Ala Pro Ala Glu Thr Leu Arg Glu
            85                  90                  95

Asp Leu His Asp Glu Leu Gly Ser Asn Glu Gly Glu Leu Ala Asn Leu
        100                 105                 110

Ser Glu Glu Phe Asn Pro Pro Glu Phe Glu Asp Asn Tyr Glu Glu Phe
    115                 120                 125

Gly Ser Thr Ser Asn Trp Asp Glu Ala Gly Arg Asn Asn Leu Asp Asp
130             135                 140

Glu Asp Ser Asp Phe Ser Arg Gln Asp Ala Ser Asn Ile Ser Leu Arg
145                 150                 155                 160

Glu His Leu Leu Asp Gln Ile Gln Leu Ala His Leu Ser Gln Arg Asp
            165                 170                 175

Met Thr Leu Val Lys Leu Leu Asp Ser Ile Asn Asp Asp Gly Tyr
        180                 185                 190

Leu Glu Gln Asp Leu Gln Glu Ile Val Glu His Leu Pro Ile Glu Leu
    195                 200                 205

Glu Val Glu Leu Leu Glu Leu Glu Thr Ala Leu Lys Leu Ile Gln Asn
210                 215                 220

Leu Asp Pro Val Gly Val Gly Ala Arg Asp Leu Arg Glu Cys Leu Leu
225                 230                 235                 240

Leu Gln Leu Gln His Leu Pro Ala Glu Thr Pro Tyr Leu Arg Thr Ala
            245                 250                 255

Met Ala Leu Ala Lys Asp His Leu Ala Leu Leu Ala Asn Lys Asp Phe
        260                 265                 270

Val Lys Leu Arg Lys Leu Leu Ser Cys Asp Glu Thr Ala Leu Lys Gly
    275                 280                 285

Ala Gln Gln Leu Ile Arg Gln Gln Asn Pro Lys Pro Gly Ser Glu Phe
290                 295                 300

Ala Thr Phe Ser His Asp His Phe Ile Gln His Asp Val Val Lys
```

```
                305                 310                 315                 320
Lys Ile Lys Gly Ile Trp Val Ala Ser Leu Asn Asp Gly Val Ile Pro
                325                 330                 335

Lys Leu Arg Ile Asn Gln Leu Tyr Ala Asp Ile Leu Lys Arg Asn Arg
            340                 345                 350

Glu Ser Ser Gly Gln Tyr Leu Gln Ser Gln Met Gln Glu Ala Lys Trp
        355                 360                 365

Met Ile Lys Asn Ile Gln Gln Arg Phe Ser Thr Ile Leu Arg Val Ser
    370                 375                 380

Gln Ala Ile Val Asp Arg Gln Arg Asn Phe Phe Glu His Gly Asp Ile
385                 390                 395                 400

Ala Met Arg Pro Leu Val Leu Arg Glu Ile Ala Glu Leu Asp Leu
                405                 410                 415

His Glu Ser Thr Val Ser Arg Val Thr Thr His Lys Tyr Met Leu Thr
                420                 425                 430

Pro Arg Gly Val Tyr Glu Leu Lys Tyr Phe Phe Gly Ser Ser Val Ala
            435                 440                 445

Thr Asp Ala Gly Gly Ser Cys Ser Ala Thr Ala Ile Arg Ala Leu Ile
        450                 455                 460

Lys Gln Met Val Ala Glu Asn Pro Lys Lys Pro Leu Ser Asp Asn
465                 470                 475                 480

Gln Ile Thr Asp Thr Leu Ala Gln Gln Gly Ile Val Val Ala Arg Arg
                485                 490                 495

Thr Ile Ala Lys Tyr Arg Glu Ser Leu Asn Ile Pro Pro Ala Asn Leu
                500                 505                 510

Arg Lys Ser Leu
        515

<210> SEQ ID NO 19
<211> LENGTH: 1920
<212> TYPE: DNA
<213> ORGANISM: Methylophilus methylotrophus
<220> FEATURE:
<221> NAME/KEY: CDS
<222> LOCATION: (1)..(1920)
<223> OTHER INFORMATION:

<400> SEQUENCE: 19 atg gca aag att atc ggt att gat ttg gga acg aca aac tca tgc gtc      48
Met Ala Lys Ile Ile Gly Ile Asp Leu Gly Thr Thr Asn Ser Cys Val
1               5                   10                  15 gcc gtg atg gaa ggt ggc aag cca cgt gtg att gag aac gct gaa ggc      96
Ala Val Met Glu Gly Gly Lys Pro Arg Val Ile Glu Asn Ala Glu Gly
            20                  25                  30 gcg cgt acc acg cct tct att att gct tac cag gaa gac ggc gaa att     144
Ala Arg Thr Thr Pro Ser Ile Ile Ala Tyr Gln Glu Asp Gly Glu Ile
        35                  40                  45 ctg gtg ggt gca cca gca aaa cgt cag gca gtg act aac ccc aaa aat     192
Leu Val Gly Ala Pro Ala Lys Arg Gln Ala Val Thr Asn Pro Lys Asn
    50                  55                  60 acc ctg ttt gcg gtg aag cgt ttg att ggc cgt cgc ttt gac gaa aaa     240
Thr Leu Phe Ala Val Lys Arg Leu Ile Gly Arg Arg Phe Asp Glu Lys
65                  70                  75                  80 gaa gtg caa aaa gac atc gac ctc atg cct tac acc att gcc aag gct     288
Glu Val Gln Lys Asp Ile Asp Leu Met Pro Tyr Thr Ile Ala Lys Ala
                85                  90                  95 gac aat ggt gac gca tgg gta gaa gtg cgt ggc aaa aaa cag gcg cca     336
Asp Asn Gly Asp Ala Trp Val Glu Val Arg Gly Lys Lys Gln Ala Pro
```

-continued

```
              100                 105                 110
cca caa att tct gcc gaa gtg ttg cgc aaa atg aag aaa act gct gaa    384
Pro Gln Ile Ser Ala Glu Val Leu Arg Lys Met Lys Lys Thr Ala Glu
        115                 120                 125 gac tac ctg ggc gaa gaa gtg acc gag gcc gtg att acc gtg ccc gct    432
Asp Tyr Leu Gly Glu Glu Val Thr Glu Ala Val Ile Thr Val Pro Ala
130                 135                 140 tac ttt aac gat agc cag cgt cag gca act aaa gat gca ggc cgt atc    480
Tyr Phe Asn Asp Ser Gln Arg Gln Ala Thr Lys Asp Ala Gly Arg Ile
145                 150                 155                 160 gct ggt ctg gaa gta aaa cgt atc atc aac gag cca acg gca gcg gca    528
Ala Gly Leu Glu Val Lys Arg Ile Ile Asn Glu Pro Thr Ala Ala Ala
                165                 170                 175 ctg gca ttt ggt ttg gac aaa cag gaa ggt gac cgc aag att gcg gta    576
Leu Ala Phe Gly Leu Asp Lys Gln Glu Gly Asp Arg Lys Ile Ala Val
            180                 185                 190 tat gac ctg ggt ggc ggc act ttc gat att tcg att att gaa att act    624
Tyr Asp Leu Gly Gly Gly Thr Phe Asp Ile Ser Ile Ile Glu Ile Thr
        195                 200                 205 gaa atc gac ggc gag cac cag ttc gaa gtg ttg tct acc aat ggt gac    672
Glu Ile Asp Gly Glu His Gln Phe Glu Val Leu Ser Thr Asn Gly Asp
    210                 215                 220 aca ttc ctc ggt ggt gaa gac ttt gat aac cgc atc atc gac ttt ttg    720
Thr Phe Leu Gly Gly Glu Asp Phe Asp Asn Arg Ile Ile Asp Phe Leu
225                 230                 235                 240 gct gac gaa ttc aag aaa gaa aac ggc ttg gac ttg cgt aac gac ttg    768
Ala Asp Glu Phe Lys Lys Glu Asn Gly Leu Asp Leu Arg Asn Asp Leu
                245                 250                 255 ctg gca aaa cag cgt ctg aaa gag gcg gcc gaa aaa gcc aag atc gaa    816
Leu Ala Lys Gln Arg Leu Lys Glu Ala Ala Glu Lys Ala Lys Ile Glu
            260                 265                 270 ttg tct ggt gca cag cag act gaa gtg aac ctg ccg tac atc acg gct    864
Leu Ser Gly Ala Gln Gln Thr Glu Val Asn Leu Pro Tyr Ile Thr Ala
        275                 280                 285 gat gcg acc ggt cct aag cac ttg gtg gtg aaa atc act cgt gcc aag    912
Asp Ala Thr Gly Pro Lys His Leu Val Val Lys Ile Thr Arg Ala Lys
    290                 295                 300 ctg gag tca ttg gtg gaa gac ctg att gag cga acc atc agc cca tgt    960
Leu Glu Ser Leu Val Glu Asp Leu Ile Glu Arg Thr Ile Ser Pro Cys
305                 310                 315                 320 aaa acg gca ttg aaa gat gca ggc gtg tct cct tca gat att tct gac   1008
Lys Thr Ala Leu Lys Asp Ala Gly Val Ser Pro Ser Asp Ile Ser Asp
                325                 330                 335 gtg att ttg gtg ggc ggt cag agc cgg atg cct aaa gtg caa gaa aaa   1056
Val Ile Leu Val Gly Gly Gln Ser Arg Met Pro Lys Val Gln Glu Lys
            340                 345                 350 gtg aaa gag att ttt ggc aag gaa cca cgt aaa gat gtg aac ccg gat   1104
Val Lys Glu Ile Phe Gly Lys Glu Pro Arg Lys Asp Val Asn Pro Asp
        355                 360                 365 gaa gcc gtg gcc gta ggt gct gcg atc cag ggc ggc gta ctg aaa ggc   1152
Glu Ala Val Ala Val Gly Ala Ala Ile Gln Gly Gly Val Leu Lys Gly
    370                 375                 380 gac gtg aaa gac gtg ttg ctg ctg gac gtg aca cca ttg tcc ctg ggt   1200
Asp Val Lys Asp Val Leu Leu Leu Asp Val Thr Pro Leu Ser Leu Gly
385                 390                 395                 400 att gaa acc ctg ggt agc gtg atg acc aag ctg atc aag aaa aac acc   1248
Ile Glu Thr Leu Gly Ser Val Met Thr Lys Leu Ile Lys Lys Asn Thr
                405                 410                 415 acg att cct acc aag gca tca caa gtg ttc tcg aca gct gaa gac aac   1296
```

```
Thr Ile Pro Thr Lys Ala Ser Gln Val Phe Ser Thr Ala Glu Asp Asn
        420                 425                 430 cag aat gcg gtg act atc cat gtg ttg caa ggt gaa cgc gaa atg gct    1344
Gln Asn Ala Val Thr Ile His Val Leu Gln Gly Glu Arg Glu Met Ala
            435                 440                 445 tcc ggc aac aag agc ctg ggc cag ttt aac ctc agc gac att cca cct    1392
Ser Gly Asn Lys Ser Leu Gly Gln Phe Asn Leu Ser Asp Ile Pro Pro
450                 455                 460 gca ccg cgt ggc atg ccg caa att gaa gtg act ttt gat atc gat gcc    1440
Ala Pro Arg Gly Met Pro Gln Ile Glu Val Thr Phe Asp Ile Asp Ala
465                 470                 475                 480 aac ggt att ttg cat gtg tct gcc aaa gac aag gcc act ggc aaa gaa    1488
Asn Gly Ile Leu His Val Ser Ala Lys Asp Lys Ala Thr Gly Lys Glu
                485                 490                 495 aac aag atc acc atc aaa gct aac tcc ggc ttg tct gaa gaa gaa att    1536
Asn Lys Ile Thr Ile Lys Ala Asn Ser Gly Leu Ser Glu Glu Glu Ile
            500                 505                 510 cag cgc atg gaa gaa gat gcg gct aaa tat gct gac gaa gac aaa aaa    1584
Gln Arg Met Glu Glu Asp Ala Ala Lys Tyr Ala Asp Glu Asp Lys Lys
        515                 520                 525 ctg cgt gaa ctg gtc gac gcc cgt aac cag gcg gac agc gtg ttg cac    1632
Leu Arg Glu Leu Val Asp Ala Arg Asn Gln Ala Asp Ser Val Leu His
    530                 535                 540 agc gtg aaa aaa tcg ttg gct gag cat ggc gac aag att gag gcc gat    1680
Ser Val Lys Lys Ser Leu Ala Glu His Gly Asp Lys Ile Glu Ala Asp
545                 550                 555                 560 gaa aaa gcc aag att gaa gac gca att aaa gac ctg gaa gcg gta gct    1728
Glu Lys Ala Lys Ile Glu Asp Ala Ile Lys Asp Leu Glu Ala Val Ala
                565                 570                 575 aaa gac ggc gac gat aaa gaa gtg att gaa gcc aag acc aat gct ttg    1776
Lys Asp Gly Asp Asp Lys Glu Val Ile Glu Ala Lys Thr Asn Ala Leu
            580                 585                 590 atg gaa gct tca caa aaa ctg ggt gaa aag gtc tat gcc gag caa cag    1824
Met Glu Ala Ser Gln Lys Leu Gly Glu Lys Val Tyr Ala Glu Gln Gln
        595                 600                 605 gca cag gcc aat acc gag agt gca caa gct gaa act gaa aaa aca gtg    1872
Ala Gln Ala Asn Thr Glu Ser Ala Gln Ala Glu Thr Glu Lys Thr Val
    610                 615                 620 gaa ggc gat gtg gtg gat gcc gag ttt gaa gaa gtg aag aaa aac taa    1920
Glu Gly Asp Val Val Asp Ala Glu Phe Glu Glu Val Lys Lys Asn
625                 630                 635

<210> SEQ ID NO 20
<211> LENGTH: 639
<212> TYPE: PRT
<213> ORGANISM: Methylophilus methylotrophus

<400> SEQUENCE: 20

Met Ala Lys Ile Ile Gly Ile Asp Leu Gly Thr Thr Asn Ser Cys Val
1               5                   10                  15

Ala Val Met Glu Gly Gly Lys Pro Arg Val Ile Glu Asn Ala Glu Gly
            20                  25                  30

Ala Arg Thr Thr Pro Ser Ile Ile Ala Tyr Gln Glu Asp Gly Glu Ile
        35                  40                  45

Leu Val Gly Ala Pro Ala Lys Arg Gln Ala Val Thr Asn Pro Lys Asn
    50                  55                  60

Thr Leu Phe Ala Val Lys Arg Leu Ile Gly Arg Arg Phe Asp Glu Lys
65                  70                  75                  80

Glu Val Gln Lys Asp Ile Asp Leu Met Pro Tyr Thr Ile Ala Lys Ala
```

-continued

```
                    85                  90                  95
Asp Asn Gly Asp Ala Trp Val Glu Val Arg Gly Lys Lys Gln Ala Pro
                100                 105                 110
Pro Gln Ile Ser Ala Glu Val Leu Arg Lys Met Lys Lys Thr Ala Glu
                115                 120                 125
Asp Tyr Leu Gly Glu Val Thr Glu Ala Val Ile Thr Val Pro Ala
                130                 135                 140
Tyr Phe Asn Asp Ser Gln Arg Gln Ala Thr Lys Asp Ala Gly Arg Ile
145                 150                 155                 160
Ala Gly Leu Glu Val Lys Arg Ile Ile Asn Glu Pro Thr Ala Ala Ala
                165                 170                 175
Leu Ala Phe Gly Leu Asp Lys Gln Glu Gly Asp Arg Lys Ile Ala Val
                180                 185                 190
Tyr Asp Leu Gly Gly Gly Thr Phe Asp Ile Ser Ile Ile Glu Ile Thr
                195                 200                 205
Glu Ile Asp Gly Glu His Gln Phe Glu Val Leu Ser Thr Asn Gly Asp
                210                 215                 220
Thr Phe Leu Gly Gly Glu Asp Phe Asp Asn Arg Ile Ile Asp Phe Leu
225                 230                 235                 240
Ala Asp Glu Phe Lys Lys Glu Asn Gly Leu Asp Leu Arg Asn Asp Leu
                245                 250                 255
Leu Ala Lys Gln Arg Leu Lys Glu Ala Ala Glu Lys Ala Lys Ile Glu
                260                 265                 270
Leu Ser Gly Ala Gln Gln Thr Glu Val Asn Leu Pro Tyr Ile Thr Ala
                275                 280                 285
Asp Ala Thr Gly Pro Lys His Leu Val Val Lys Ile Thr Arg Ala Lys
                290                 295                 300
Leu Glu Ser Leu Val Glu Asp Leu Ile Glu Arg Thr Ile Ser Pro Cys
305                 310                 315                 320
Lys Thr Ala Leu Lys Asp Ala Gly Val Ser Pro Ser Asp Ile Ser Asp
                325                 330                 335
Val Ile Leu Val Gly Gly Gln Ser Arg Met Pro Lys Val Gln Glu Lys
                340                 345                 350
Val Lys Glu Ile Phe Gly Lys Glu Pro Arg Lys Asp Val Asn Pro Asp
                355                 360                 365
Glu Ala Val Ala Val Gly Ala Ala Ile Gln Gly Gly Val Leu Lys Gly
                370                 375                 380
Asp Val Lys Asp Val Leu Leu Leu Asp Val Thr Pro Leu Ser Leu Gly
385                 390                 395                 400
Ile Glu Thr Leu Gly Ser Val Met Thr Lys Leu Ile Lys Lys Asn Thr
                405                 410                 415
Thr Ile Pro Thr Lys Ala Ser Gln Val Phe Ser Thr Ala Glu Asp Asn
                420                 425                 430
Gln Asn Ala Val Thr Ile His Val Leu Gln Gly Glu Arg Glu Met Ala
                435                 440                 445
Ser Gly Asn Lys Ser Leu Gly Gln Phe Asn Leu Ser Asp Ile Pro Pro
                450                 455                 460
Ala Pro Arg Gly Met Pro Gln Ile Glu Val Thr Phe Asp Ile Asp Ala
465                 470                 475                 480
Asn Gly Ile Leu His Val Ser Ala Lys Asp Lys Ala Thr Gly Lys Glu
                485                 490                 495
Asn Lys Ile Thr Ile Lys Ala Asn Ser Gly Leu Ser Glu Glu Glu Ile
                500                 505                 510
```

-continued

```
Gln Arg Met Glu Glu Asp Ala Ala Lys Tyr Ala Asp Glu Asp Lys Lys
        515                 520                 525

Leu Arg Glu Leu Val Asp Ala Arg Asn Gln Ala Asp Ser Val Leu His
    530                 535                 540

Ser Val Lys Lys Ser Leu Ala Glu His Gly Asp Lys Ile Glu Ala Asp
545                 550                 555                 560

Glu Lys Ala Lys Ile Glu Asp Ala Ile Lys Asp Leu Glu Ala Val Ala
                565                 570                 575

Lys Asp Gly Asp Asp Lys Glu Val Ile Glu Ala Lys Thr Asn Ala Leu
            580                 585                 590

Met Glu Ala Ser Gln Lys Leu Gly Glu Lys Val Tyr Ala Glu Gln Gln
        595                 600                 605

Ala Gln Ala Asn Thr Glu Ser Ala Gln Ala Glu Thr Glu Lys Thr Val
    610                 615                 620

Glu Gly Asp Val Val Asp Ala Glu Phe Glu Glu Val Lys Lys Asn
625                 630                 635

<210> SEQ ID NO 21
<211> LENGTH: 1131
<212> TYPE: DNA
<213> ORGANISM: Methylophilus methylotrophus
<220> FEATURE:
<221> NAME/KEY: CDS
<222> LOCATION: (1)..(1131)
<223> OTHER INFORMATION:

<400> SEQUENCE: 21 atg gca gct gca aaa aaa gat tat tac gaa gtg tta ggt gta aac cgc         48
Met Ala Ala Ala Lys Lys Asp Tyr Tyr Glu Val Leu Gly Val Asn Arg
1               5                   10                  15 gac gcc agc gaa gag gaa att aaa aaa gcc ttt aaa aaa ctg gcc atg         96
Asp Ala Ser Glu Glu Glu Ile Lys Lys Ala Phe Lys Lys Leu Ala Met
            20                  25                  30 aag ttt cac ccg gac cgc aac ccg gat aac ccc aaa gcc gaa gaa agc        144
Lys Phe His Pro Asp Arg Asn Pro Asp Asn Pro Lys Ala Glu Glu Ser
        35                  40                  45 ttt aag gaa gcc aaa gag gct tat gag ata ttg agt gac gag cag aag        192
Phe Lys Glu Ala Lys Glu Ala Tyr Glu Ile Leu Ser Asp Glu Gln Lys
    50                  55                  60 cgc gct gct tat gac caa tat ggc cat gcc ggc gta gac ccc agc atg        240
Arg Ala Ala Tyr Asp Gln Tyr Gly His Ala Gly Val Asp Pro Ser Met
65                  70                  75                  80 ggc ggt ggc ggt gga ttt ggc gga ttc aat tct ggc aac ttc agt gac        288
Gly Gly Gly Gly Gly Phe Gly Gly Phe Asn Ser Gly Asn Phe Ser Asp
                85                  90                  95 gcg ttt ggc gat att ttt ggg gat att ttc ggt ggt gcg cgc aac cag        336
Ala Phe Gly Asp Ile Phe Gly Asp Ile Phe Gly Gly Ala Arg Asn Gln
            100                 105                 110 cgc tcg aat gtg tac cgt ggt gcg gat tta cgt tac aac ctg gaa att        384
Arg Ser Asn Val Tyr Arg Gly Ala Asp Leu Arg Tyr Asn Leu Glu Ile
        115                 120                 125 tcg ctg gaa gat gcg gcc aaa ggg act gag acc aaa atc cgt att ccg        432
Ser Leu Glu Asp Ala Ala Lys Gly Thr Glu Thr Lys Ile Arg Ile Pro
    130                 135                 140 gta cag acc act tgt gaa acc tgt cac ggt tca ggc gcg cgt cca ggg        480
Val Gln Thr Thr Cys Glu Thr Cys His Gly Ser Gly Ala Arg Pro Gly
145                 150                 155                 160 aca tcc cct gtg act tgt acc acc tgt aac ggt cac ggc cag gta cgt        528
Thr Ser Pro Val Thr Cys Thr Thr Cys Asn Gly His Gly Gln Val Arg
```

```
                  165                 170                 175
atg caa cag ggt ttt ttc tct gta cag caa acc tgt ccc aaa tgt cat       576
Met Gln Gln Gly Phe Phe Ser Val Gln Gln Thr Cys Pro Lys Cys His
            180                 185                 190 ggc acc ggc aaa atg gtg aaa gag cct tgc cca act tgc cat ggc ggt       624
Gly Thr Gly Lys Met Val Lys Glu Pro Cys Pro Thr Cys His Gly Gly
        195                 200                 205 ggt cgc gtc aaa cag aat aaa acg ctg aat gtg aag att cca gcg ggt       672
Gly Arg Val Lys Gln Asn Lys Thr Leu Asn Val Lys Ile Pro Ala Gly
    210                 215                 220 gtc gac gag ggg gat cgt atc cgc ctc agc ggt gag ggt gaa gct ggc       720
Val Asp Glu Gly Asp Arg Ile Arg Leu Ser Gly Glu Gly Glu Ala Gly
225                 230                 235                 240 gtc aat ggc ggc cca acg ggt gat ttg tat gtg gtg gtg cat ctc aag       768
Val Asn Gly Gly Pro Thr Gly Asp Leu Tyr Val Val Val His Leu Lys
                245                 250                 255 gaa cac ccg att ttc cag cgc gaa ggt gca aac ctg cat tgt gaa atg       816
Glu His Pro Ile Phe Gln Arg Glu Gly Ala Asn Leu His Cys Glu Met
            260                 265                 270 cct atc agc ttt agt acc gcg gcc tta ggc ggc gaa att gaa gtg ccg       864
Pro Ile Ser Phe Ser Thr Ala Ala Leu Gly Gly Glu Ile Glu Val Pro
        275                 280                 285 acg ctg gat ggt gca gcc aag atg aag ata ccg gct gaa acg caa aca       912
Thr Leu Asp Gly Ala Ala Lys Met Lys Ile Pro Ala Glu Thr Gln Thr
    290                 295                 300 ggc agt gta ttc cgt ttg cgc ggc aag ggt atc aag ccc tta cgc tcc       960
Gly Ser Val Phe Arg Leu Arg Gly Lys Gly Ile Lys Pro Leu Arg Ser
305                 310                 315                 320 agc gaa tat ggt gat ttg atg gtg cat gtg gtc gtt gaa acg cca gtg      1008
Ser Glu Tyr Gly Asp Leu Met Val His Val Val Val Glu Thr Pro Val
                325                 330                 335 cgc ctg aca gaa aag cag aaa gaa ctg ttg cgt gag ttt gaa agt agt      1056
Arg Leu Thr Glu Lys Gln Lys Glu Leu Leu Arg Glu Phe Glu Ser Ser
            340                 345                 350 act cag gca gat gcg gga aaa cat agc ccc aag aat aaa agc tgg gta      1104
Thr Gln Ala Asp Ala Gly Lys His Ser Pro Lys Asn Lys Ser Trp Val
        355                 360                 365 gat aaa gcc cgc gat ttt ttt agc tag                                  1131
Asp Lys Ala Arg Asp Phe Phe Ser
    370                 375

<210> SEQ ID NO 22
<211> LENGTH: 376
<212> TYPE: PRT
<213> ORGANISM: Methylophilus methylotrophus

<400> SEQUENCE: 22

Met Ala Ala Ala Lys Lys Asp Tyr Tyr Glu Val Leu Gly Val Asn Arg
1               5                   10                  15

Asp Ala Ser Glu Glu Ile Lys Lys Ala Phe Lys Lys Leu Ala Met
            20                  25                  30

Lys Phe His Pro Asp Arg Asn Pro Asp Asn Pro Lys Ala Glu Glu Ser
        35                  40                  45

Phe Lys Glu Ala Lys Glu Ala Tyr Glu Ile Leu Ser Asp Glu Gln Lys
    50                  55                  60

Arg Ala Ala Tyr Asp Gln Tyr Gly His Ala Gly Val Asp Pro Ser Met
65                  70                  75                  80

Gly Gly Gly Gly Gly Phe Gly Gly Phe Asn Ser Gly Asn Phe Ser Asp
                85                  90                  95
```

```
Ala Phe Gly Asp Ile Phe Gly Asp Ile Phe Gly Gly Ala Arg Asn Gln
            100                 105                 110

Arg Ser Asn Val Tyr Arg Gly Ala Asp Leu Arg Tyr Asn Leu Glu Ile
        115                 120                 125

Ser Leu Glu Asp Ala Ala Lys Gly Thr Glu Thr Lys Ile Arg Ile Pro
    130                 135                 140

Val Gln Thr Thr Cys Glu Thr Cys His Gly Ser Gly Ala Arg Pro Gly
145                 150                 155                 160

Thr Ser Pro Val Thr Cys Thr Cys Asn Gly His Gly Gln Val Arg
                165                 170                 175

Met Gln Gln Gly Phe Phe Ser Val Gln Gln Thr Cys Pro Lys Cys His
            180                 185                 190

Gly Thr Gly Lys Met Val Lys Glu Pro Cys Pro Thr Cys His Gly Gly
        195                 200                 205

Gly Arg Val Lys Gln Asn Lys Thr Leu Asn Val Lys Ile Pro Ala Gly
    210                 215                 220

Val Asp Glu Gly Asp Arg Ile Arg Leu Ser Gly Glu Gly Glu Ala Gly
225                 230                 235                 240

Val Asn Gly Gly Pro Thr Gly Asp Leu Tyr Val Val His Leu Lys
                245                 250                 255

Glu His Pro Ile Phe Gln Arg Glu Gly Ala Asn Leu His Cys Glu Met
            260                 265                 270

Pro Ile Ser Phe Ser Thr Ala Ala Leu Gly Gly Glu Ile Glu Val Pro
        275                 280                 285

Thr Leu Asp Gly Ala Ala Lys Met Lys Ile Pro Ala Glu Thr Gln Thr
    290                 295                 300

Gly Ser Val Phe Arg Leu Arg Gly Lys Gly Ile Lys Pro Leu Arg Ser
305                 310                 315                 320

Ser Glu Tyr Gly Asp Leu Met Val His Val Val Glu Thr Pro Val
                325                 330                 335

Arg Leu Thr Glu Lys Gln Lys Glu Leu Leu Arg Glu Phe Glu Ser Ser
            340                 345                 350

Thr Gln Ala Asp Ala Gly Lys His Ser Pro Lys Asn Lys Ser Trp Val
        355                 360                 365

Asp Lys Ala Arg Asp Phe Phe Ser
    370                 375

<210> SEQ ID NO 23
<211> LENGTH: 1890
<212> TYPE: DNA
<213> ORGANISM: Methylophilus methylotrophus
<220> FEATURE:
<221> NAME/KEY: CDS
<222> LOCATION: (1)..(1890)
<223> OTHER INFORMATION:

<400> SEQUENCE: 23 atg gcc tta tta cag att tct gaa ccc gga caa tcc cca gca ccc cat     48
Met Ala Leu Leu Gln Ile Ser Glu Pro Gly Gln Ser Pro Ala Pro His
1               5                   10                  15 cag cat aag ctg gcc att ggc ata gac ctg ggt acg acc aac tcc ctg     96
Gln His Lys Leu Ala Ile Gly Ile Asp Leu Gly Thr Thr Asn Ser Leu
            20                  25                  30 gtc gcc act gtg cgt agc ggc atg agt aca gtg ttg cat gac gaa cat    144
Val Ala Thr Val Arg Ser Gly Met Ser Thr Val Leu His Asp Glu His
        35                  40                  45
```

```
ggt cat gca ttg cta cct tct gtt gtg cgt tac ctc aat gac gcc gta       192
Gly His Ala Leu Leu Pro Ser Val Val Arg Tyr Leu Asn Asp Ala Val
 50                  55                  60 att gtc ggt cac gag gcg cag gct gca caa agc cag gac ccg gtg aat       240
Ile Val Gly His Glu Ala Gln Ala Ala Gln Ser Gln Asp Pro Val Asn
 65                  70                  75                  80 acc atc gtg tcg gtc aaa cgc ttt atg ggg cgt gca ttg cat gac atc       288
Thr Ile Val Ser Val Lys Arg Phe Met Gly Arg Ala Leu His Asp Ile
                 85                  90                  95 acc gat aga gcg cat atc ccc tac cac ttt gtt gaa aat gac agc tca       336
Thr Asp Arg Ala His Ile Pro Tyr His Phe Val Glu Asn Asp Ser Ser
            100                 105                 110 caa ggc atg ctg gaa ctc aaa acc cgc gca ggg ttg aaa agc ccg gtg       384
Gln Gly Met Leu Glu Leu Lys Thr Arg Ala Gly Leu Lys Ser Pro Val
        115                 120                 125 gag att tct gcc gaa atc ctc aaa aca ctc aaa gcc cgt gcc gaa aaa       432
Glu Ile Ser Ala Glu Ile Leu Lys Thr Leu Lys Ala Arg Ala Glu Lys
130                 135                 140 gct tta ggc ggt gaa ctc acg ggg gcc gtc att acc gtc ccc gcc tat       480
Ala Leu Gly Gly Glu Leu Thr Gly Ala Val Ile Thr Val Pro Ala Tyr
145                 150                 155                 160 ttt gac gat gcc cag cgc cag gcc acc aaa gat gct gca cgc ctc gca       528
Phe Asp Asp Ala Gln Arg Gln Ala Thr Lys Asp Ala Ala Arg Leu Ala
                165                 170                 175 ggg ttg cat gta ttg cgc ctg ctc aat gag ccg acg gca gcg gca gtc       576
Gly Leu His Val Leu Arg Leu Leu Asn Glu Pro Thr Ala Ala Ala Val
            180                 185                 190 gcc tat ggt ctg gat aat gcc gcc gaa ggt gtc tat gtc att tat gac       624
Ala Tyr Gly Leu Asp Asn Ala Ala Glu Gly Val Tyr Val Ile Tyr Asp
        195                 200                 205 ctg ggt ggt ggc acc ttt gat att tct atc tta cgc ttg agc aaa ggc       672
Leu Gly Gly Gly Thr Phe Asp Ile Ser Ile Leu Arg Leu Ser Lys Gly
210                 215                 220 gta ttt gag gta ctg gcc acc aat ggc gac tca gcc ctg ggg gga gat       720
Val Phe Glu Val Leu Ala Thr Asn Gly Asp Ser Ala Leu Gly Gly Asp
225                 230                 235                 240 gac ttc gat cat cgc att tat tgc tgg gta ctg gac cag gta cgc agc       768
Asp Phe Asp His Arg Ile Tyr Cys Trp Val Leu Asp Gln Val Arg Ser
                245                 250                 255 aag acc aaa gac ttc aaa ccg ctc acc gaa gaa gat aca cgc ctg ttg       816
Lys Thr Lys Asp Phe Lys Pro Leu Thr Glu Glu Asp Thr Arg Leu Leu
            260                 265                 270 ctg act aag tca cgc cag gcc aaa gaa tgg ctg aca gat aac cac gaa       864
Leu Thr Lys Ser Arg Gln Ala Lys Glu Trp Leu Thr Asp Asn His Glu
        275                 280                 285 gcc aat att gtc tgc aaa ctg agt aat ggt gca ctg gtt gat gaa acc       912
Ala Asn Ile Val Cys Lys Leu Ser Asn Gly Ala Leu Val Asp Glu Thr
290                 295                 300 ttg act gac agc cag ttt gtc gca ctg act gaa cac ctg gtc atc aag       960
Leu Thr Asp Ser Gln Phe Val Ala Leu Thr Glu His Leu Val Ile Lys
305                 310                 315                 320 acg ctc agc cct acc cgc aaa gcc atg cgt gat gca ggc ctg aac att      1008
Thr Leu Ser Pro Thr Arg Lys Ala Met Arg Asp Ala Gly Leu Asn Ile
                325                 330                 335 gca gaa atc aaa ggc gtg gta ctg gtc ggt ggc gcc acc cgt atg ccg      1056
Ala Glu Ile Lys Gly Val Val Leu Val Gly Gly Ala Thr Arg Met Pro
            340                 345                 350 cat atc cgc cat gcg gta cag gct ttt ttc gag cag gaa ccg ctg acc      1104
His Ile Arg His Ala Val Gln Ala Phe Phe Glu Gln Glu Pro Leu Thr
        355                 360                 365
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aac | ctt | gac | ccg | gat | aaa | gtc | gtg | gca | ctc | ggt | gcc | gct | atc | cag | gcc | 1152 |
| Asn | Leu | Asp | Pro | Asp | Lys | Val | Val | Ala | Leu | Gly | Ala | Ala | Ile | Gln | Ala |      |
|     | 370 |     |     |     | 375 |     |     |     | 380 |     |     |     |     |     |     |      |
| aat | gtg | ctg | gca | gga | aac | cgc | agt | gac | gaa | gaa | tta | ctg | tta | ctg | gac | 1200 |
| Asn | Val | Leu | Ala | Gly | Asn | Arg | Ser | Asp | Glu | Glu | Leu | Leu | Leu | Leu | Asp |      |
| 385 |     |     |     |     | 390 |     |     |     |     | 395 |     |     |     |     | 400 |      |
| gtg | acc | ccg | ctc | tca | ctg | ggg | ctg | gaa | acc | atg | ggc | gga | ctg | gtt | gaa | 1248 |
| Val | Thr | Pro | Leu | Ser | Leu | Gly | Leu | Glu | Thr | Met | Gly | Gly | Leu | Val | Glu |      |
|     |     |     |     | 405 |     |     |     |     | 410 |     |     |     |     | 415 |     |      |
| aaa | gtt | att | ccg | cgc | aac | tct | aca | ctg | ccg | att | gca | cgt | gca | cag | gac | 1296 |
| Lys | Val | Ile | Pro | Arg | Asn | Ser | Thr | Leu | Pro | Ile | Ala | Arg | Ala | Gln | Asp |      |
|     |     | 420 |     |     |     |     | 425 |     |     |     |     | 430 |     |     |     |      |
| ttc | acc | act | tac | aag | gat | ggc | cag | acc | gcc | atg | gcc | att | cat | gtt | gtg | 1344 |
| Phe | Thr | Thr | Tyr | Lys | Asp | Gly | Gln | Thr | Ala | Met | Ala | Ile | His | Val | Val |      |
|     |     |     | 435 |     |     |     |     | 440 |     |     |     |     | 445 |     |     |      |
| caa | ggc | gag | cgt | gaa | ctg | gtc | agt | gac | tgc | cgc | tcg | ctg | gca | cgc | ttt | 1392 |
| Gln | Gly | Glu | Arg | Glu | Leu | Val | Ser | Asp | Cys | Arg | Ser | Leu | Ala | Arg | Phe |      |
|     | 450 |     |     |     |     | 455 |     |     |     |     | 460 |     |     |     |     |      |
| gaa | ctg | cgt | ggc | att | ccc | cca | atg | gca | gcc | ggc | gca | gcg | cgt | atc | cgc | 1440 |
| Glu | Leu | Arg | Gly | Ile | Pro | Pro | Met | Ala | Ala | Gly | Ala | Ala | Arg | Ile | Arg |      |
| 465 |     |     |     |     | 470 |     |     |     |     | 475 |     |     |     |     | 480 |      |
| gtc | act | ttc | cag | gta | gat | gct | gat | ggg | ctg | cta | tca | gtc | agt | gca | cgc | 1488 |
| Val | Thr | Phe | Gln | Val | Asp | Ala | Asp | Gly | Leu | Leu | Ser | Val | Ser | Ala | Arg |      |
|     |     |     |     | 485 |     |     |     |     | 490 |     |     |     |     | 495 |     |      |
| gaa | caa | acc | agc | ggc | ata | gag | gcc | aac | atc | acg | gtc | aag | ccc | tct | tat | 1536 |
| Glu | Gln | Thr | Ser | Gly | Ile | Glu | Ala | Asn | Ile | Thr | Val | Lys | Pro | Ser | Tyr |      |
|     |     |     | 500 |     |     |     |     | 505 |     |     |     |     | 510 |     |     |      |
| ggc | ctc | agt | gaa | gac | cag | att | agc | ggt | atg | ctg | aaa | gat | tcg | ttt | ggt | 1584 |
| Gly | Leu | Ser | Glu | Asp | Gln | Ile | Ser | Gly | Met | Leu | Lys | Asp | Ser | Phe | Gly |      |
|     |     | 515 |     |     |     |     | 520 |     |     |     |     | 525 |     |     |     |      |
| gct | gct | gag | agt | gac | aaa | caa | gca | cgc | atg | ctg | cgt | gaa | gct | gtt | gtg | 1632 |
| Ala | Ala | Glu | Ser | Asp | Lys | Gln | Ala | Arg | Met | Leu | Arg | Glu | Ala | Val | Val |      |
|     |     | 530 |     |     |     |     | 535 |     |     |     |     | 540 |     |     |     |      |
| gat | gct | caa | cgc | ctg | gtc | gag | gcg | att | caa | gca | gca | ctg | gca | gaa | gat | 1680 |
| Asp | Ala | Gln | Arg | Leu | Val | Glu | Ala | Ile | Gln | Ala | Ala | Leu | Ala | Glu | Asp |      |
| 545 |     |     |     |     | 550 |     |     |     |     | 555 |     |     |     |     | 560 |      |
| gga | gag | acg | tta | cta | tct | gct | gac | gaa | cgt | cag | cag | ata | aac | gcc | cat | 1728 |
| Gly | Glu | Thr | Leu | Leu | Ser | Ala | Asp | Glu | Arg | Gln | Gln | Ile | Asn | Ala | His |      |
|     |     |     |     | 565 |     |     |     |     | 570 |     |     |     |     | 575 |     |      |
| ata | gac | acc | tta | ttg | gcc | ttg | tgc | cag | ggc | gac | gat | agc | cag | gcc | gtt | 1776 |
| Ile | Asp | Thr | Leu | Leu | Ala | Leu | Cys | Gln | Gly | Asp | Asp | Ser | Gln | Ala | Val |      |
|     |     |     | 580 |     |     |     |     | 585 |     |     |     |     | 590 |     |     |      |
| aaa | cag | gct | act | gaa | gca | ctg | aac | cat | gcc | acc | gag | gca | ttt | gct | gcc | 1824 |
| Lys | Gln | Ala | Thr | Glu | Ala | Leu | Asn | His | Ala | Thr | Glu | Ala | Phe | Ala | Ala |      |
|     |     | 595 |     |     |     |     | 600 |     |     |     |     | 605 |     |     |     |      |
| aag | cgc | atg | gat | gcc | tcg | gta | caa | aaa | gcc | ctg | gcc | ggt | aaa | aac | ctg | 1872 |
| Lys | Arg | Met | Asp | Ala | Ser | Val | Gln | Lys | Ala | Leu | Ala | Gly | Lys | Asn | Leu |      |
|     | 610 |     |     |     |     | 615 |     |     |     |     | 620 |     |     |     |     |      |
| gat | tca | ctg | gaa | cta | tga |     |     |     |     |     |     |     |     |     |     | 1890 |
| Asp | Ser | Leu | Glu | Leu |     |     |     |     |     |     |     |     |     |     |     |      |
| 625 |     |     |     |     |     |     |     |     |     |     |     |     |     |     |     |      |

<210> SEQ ID NO 24
<211> LENGTH: 629
<212> TYPE: PRT
<213> ORGANISM: Methylophilus methylotrophus

<400> SEQUENCE: 24

Met Ala Leu Leu Gln Ile Ser Glu Pro Gly Gln Ser Pro Ala Pro His
1               5                   10                  15

```
Gln His Lys Leu Ala Ile Gly Ile Asp Leu Gly Thr Thr Asn Ser Leu
             20                  25                  30
Val Ala Thr Val Arg Ser Gly Met Ser Thr Val Leu His Asp Glu His
             35                  40                  45
Gly His Ala Leu Leu Pro Ser Val Arg Tyr Leu Asn Asp Ala Val
             50                  55                  60
Ile Val Gly His Glu Ala Gln Ala Gln Ser Gln Asp Pro Val Asn
 65              70                  75                  80
Thr Ile Val Ser Val Lys Arg Phe Met Gly Arg Ala Leu His Asp Ile
                 85                  90                  95
Thr Asp Arg Ala His Ile Pro Tyr His Phe Val Glu Asn Asp Ser Ser
            100                 105                 110
Gln Gly Met Leu Glu Leu Lys Thr Arg Ala Gly Leu Lys Ser Pro Val
            115                 120                 125
Glu Ile Ser Ala Glu Ile Leu Lys Thr Leu Lys Ala Arg Ala Glu Lys
130                 135                 140
Ala Leu Gly Gly Glu Leu Thr Gly Ala Val Ile Thr Val Pro Ala Tyr
145                 150                 155                 160
Phe Asp Asp Ala Gln Arg Gln Ala Thr Lys Asp Ala Ala Arg Leu Ala
                165                 170                 175
Gly Leu His Val Leu Arg Leu Leu Asn Glu Pro Thr Ala Ala Val
                180                 185                 190
Ala Tyr Gly Leu Asp Asn Ala Ala Glu Gly Val Tyr Val Ile Tyr Asp
        195                 200                 205
Leu Gly Gly Gly Thr Phe Asp Ile Ser Ile Leu Arg Leu Ser Lys Gly
    210                 215                 220
Val Phe Glu Val Leu Ala Thr Asn Gly Asp Ser Ala Leu Gly Gly Asp
225                 230                 235                 240
Asp Phe Asp His Arg Ile Tyr Cys Trp Val Leu Asp Gln Val Arg Ser
                245                 250                 255
Lys Thr Lys Asp Phe Lys Pro Leu Thr Glu Glu Asp Thr Arg Leu Leu
            260                 265                 270
Leu Thr Lys Ser Arg Gln Ala Lys Glu Trp Leu Thr Asp Asn His Glu
    275                 280                 285
Ala Asn Ile Val Cys Lys Leu Ser Asn Gly Ala Leu Val Asp Glu Thr
290                 295                 300
Leu Thr Asp Ser Gln Phe Val Ala Leu Thr Glu His Leu Val Ile Lys
305                 310                 315                 320
Thr Leu Ser Pro Thr Arg Lys Ala Met Arg Asp Ala Gly Leu Asn Ile
                325                 330                 335
Ala Glu Ile Lys Gly Val Val Leu Val Gly Gly Ala Thr Arg Met Pro
            340                 345                 350
His Ile Arg His Ala Val Gln Ala Phe Phe Glu Gln Glu Pro Leu Thr
    355                 360                 365
Asn Leu Asp Pro Asp Lys Val Val Ala Leu Gly Ala Ala Ile Gln Ala
370                 375                 380
Asn Val Leu Ala Gly Asn Arg Ser Asp Glu Glu Leu Leu Leu Leu Asp
385                 390                 395                 400
Val Thr Pro Leu Ser Leu Gly Leu Glu Thr Met Gly Gly Leu Val Glu
                405                 410                 415
Lys Val Ile Pro Arg Asn Ser Thr Leu Pro Ile Ala Arg Ala Gln Asp
            420                 425                 430
```

```
Phe Thr Thr Tyr Lys Asp Gly Gln Thr Ala Met Ala Ile His Val Val
        435                 440                 445

Gln Gly Glu Arg Glu Leu Val Ser Asp Cys Arg Ser Leu Ala Arg Phe
        450                 455                 460

Glu Leu Arg Gly Ile Pro Pro Met Ala Gly Ala Ala Arg Ile Arg
465                 470                 475                 480

Val Thr Phe Gln Val Asp Ala Asp Gly Leu Leu Ser Val Ser Ala Arg
                485                 490                 495

Glu Gln Thr Ser Gly Ile Glu Ala Asn Ile Thr Val Lys Pro Ser Tyr
                500                 505                 510

Gly Leu Ser Glu Asp Gln Ile Ser Gly Met Leu Lys Asp Ser Phe Gly
        515                 520                 525

Ala Ala Glu Ser Asp Lys Gln Ala Arg Met Leu Arg Glu Ala Val Val
        530                 535                 540

Asp Ala Gln Arg Leu Val Glu Ala Ile Gln Ala Ala Leu Ala Glu Asp
545                 550                 555                 560

Gly Glu Thr Leu Leu Ser Ala Asp Glu Arg Gln Gln Ile Asn Ala His
                565                 570                 575

Ile Asp Thr Leu Leu Ala Leu Cys Gln Gly Asp Asp Ser Gln Ala Val
                580                 585                 590

Lys Gln Ala Thr Glu Ala Leu Asn His Ala Thr Glu Ala Phe Ala Ala
        595                 600                 605

Lys Arg Met Asp Ala Ser Val Gln Lys Ala Leu Ala Gly Lys Asn Leu
        610                 615                 620

Asp Ser Leu Glu Leu
625

<210> SEQ ID NO 25
<211> LENGTH: 513
<212> TYPE: DNA
<213> ORGANISM: Methylophilus methylotrophus
<220> FEATURE:
<221> NAME/KEY: CDS
<222> LOCATION: (1)..(513)
<223> OTHER INFORMATION:

<400> SEQUENCE: 25 atg caa aac tac ttc gca ctg ttt caa ctg cca cag caa ttt gag tta      48
Met Gln Asn Tyr Phe Ala Leu Phe Gln Leu Pro Gln Gln Phe Glu Leu
1                 5                  10                  15 gat cta act caa ctg gat agc cag tac cgt aaa tta caa gcc gaa gtg      96
Asp Leu Thr Gln Leu Asp Ser Gln Tyr Arg Lys Leu Gln Ala Glu Val
            20                  25                  30 cat ccc gat aaa ttt gtg agt gcc tca cct gcc gaa cgc atg cac tca     144
His Pro Asp Lys Phe Val Ser Ala Ser Pro Ala Glu Arg Met His Ser
        35                  40                  45 atg cag atg gcg acg ctg gca aat gaa gct tac caa acg ctt aaa cac     192
Met Gln Met Ala Thr Leu Ala Asn Glu Ala Tyr Gln Thr Leu Lys His
    50                  55                  60 ccc acc gcc cgt gca cgc tac ctg ttg caa ctc cag ggt atc act aca     240
Pro Thr Ala Arg Ala Arg Tyr Leu Leu Gln Leu Gln Gly Ile Thr Thr
65                  70                  75                  80 gat gaa gaa aac aac act gcc atg ccc gct gat ttt tta atg gca caa     288
Asp Glu Glu Asn Asn Thr Ala Met Pro Ala Asp Phe Leu Met Ala Gln
                85                  90                  95 atg gag tgg cgc gag gcc att gac gat gcc aag tac agc aag gat atc     336
Met Glu Trp Arg Glu Ala Ile Asp Asp Ala Lys Tyr Ser Lys Asp Ile
            100                 105                 110
```

| | | |
|---|---|---|
| gct gca ctg gat acc tta ttg aag gat atg cgc gcg caa gcc aca act<br>Ala Ala Leu Asp Thr Leu Leu Lys Asp Met Arg Ala Gln Ala Thr Thr<br>115                           120                       125 | | 384 |
| ttg cag cag caa gtc gca aca gag atc gag aca gcg ccc acc cta gct<br>Leu Gln Gln Gln Val Ala Thr Glu Ile Glu Thr Ala Pro Thr Leu Ala<br>    130                      135                       140 | | 432 |
| gca ctc acc gta cgc aaa ttg cgt ttt att gat aaa gtg agt gaa gat<br>Ala Leu Thr Val Arg Lys Leu Arg Phe Ile Asp Lys Val Ser Glu Asp<br>145                       150                       155                       160 | | 480 |
| gtg aat caa ctg atc gct cag ttg gaa gat tag<br>Val Asn Gln Leu Ile Ala Gln Leu Glu Asp<br>                165                       170 | | 513 |

<210> SEQ ID NO 26
<211> LENGTH: 170
<212> TYPE: PRT
<213> ORGANISM: Methylophilus methylotrophus

<400> SEQUENCE: 26

Met Gln Asn Tyr Phe Ala Leu Phe Gln Leu Pro Gln Gln Phe Glu Leu
1               5                   10                  15

Asp Leu Thr Gln Leu Asp Ser Gln Tyr Arg Lys Leu Gln Ala Glu Val
            20                  25                  30

His Pro Asp Lys Phe Val Ser Ala Ser Pro Ala Glu Arg Met His Ser
        35                  40                  45

Met Gln Met Ala Thr Leu Ala Asn Glu Ala Tyr Gln Thr Leu Lys His
    50                  55                  60

Pro Thr Ala Arg Ala Arg Tyr Leu Leu Gln Leu Gln Gly Ile Thr Thr
65                  70                  75                  80

Asp Glu Glu Asn Asn Thr Ala Met Pro Ala Asp Phe Leu Met Ala Gln
                85                  90                  95

Met Glu Trp Arg Glu Ala Ile Asp Asp Ala Lys Tyr Ser Lys Asp Ile
            100                 105                 110

Ala Ala Leu Asp Thr Leu Leu Lys Asp Met Arg Ala Gln Ala Thr Thr
        115                 120                 125

Leu Gln Gln Gln Val Ala Thr Glu Ile Glu Thr Ala Pro Thr Leu Ala
    130                 135                 140

Ala Leu Thr Val Arg Lys Leu Arg Phe Ile Asp Lys Val Ser Glu Asp
145                 150                 155                 160

Val Asn Gln Leu Ile Ala Gln Leu Glu Asp
                165                 170

<210> SEQ ID NO 27
<211> LENGTH: 1638
<212> TYPE: DNA
<213> ORGANISM: Methylophilus methylotrophus
<220> FEATURE:
<221> NAME/KEY: CDS
<222> LOCATION: (1)..(1638)
<223> OTHER INFORMATION:

<400> SEQUENCE: 27

| | | |
|---|---|---|
| atg gca gct aaa gac gta aga ttt ggt gat gac gtt cgc caa aaa atg<br>Met Ala Ala Lys Asp Val Arg Phe Gly Asp Asp Val Arg Gln Lys Met<br>1               5                       10                       15 | | 48 |
| gta aat ggc gtt aac gta ttg gct aac gct gtg cgc gta act ttg ggc<br>Val Asn Gly Val Asn Val Leu Ala Asn Ala Val Arg Val Thr Leu Gly<br>                20                       25                       30 | | 96 |
| cct aaa ggc cgt aac gtg gta ttg gag cgt tct ttt ggc gcg cca acc<br>Pro Lys Gly Arg Asn Val Val Leu Glu Arg Ser Phe Gly Ala Pro Thr | | 144 |

-continued

```
            35                  40                  45
atc act aaa gac ggt gtg tct gtg gct aaa gaa atc gaa ttg aaa gac       192
Ile Thr Lys Asp Gly Val Ser Val Ala Lys Glu Ile Glu Leu Lys Asp
         50                  55                  60 aaa ttc gaa aac atg ggc gca cag atg gtg aaa gaa gtg gct tct aaa       240
Lys Phe Glu Asn Met Gly Ala Gln Met Val Lys Glu Val Ala Ser Lys
 65                  70                  75                  80 acc aac gac atc gct ggt gac ggt aca acg act gcg act gtg ttg gca       288
Thr Asn Asp Ile Ala Gly Asp Gly Thr Thr Thr Ala Thr Val Leu Ala
                 85                  90                  95 caa gcg atc atc cgc gaa ggc atg aaa tct gtg gct gct ggc atg aac       336
Gln Ala Ile Ile Arg Glu Gly Met Lys Ser Val Ala Ala Gly Met Asn
            100                 105                 110 cca atg gac ctg aag cgc ggt atc gac aaa gcg gtt gaa gcg gcg att       384
Pro Met Asp Leu Lys Arg Gly Ile Asp Lys Ala Val Glu Ala Ala Ile
        115                 120                 125 gct gaa ttg aaa gtg caa tcc aaa ccc tgt acg acc agc aaa gaa atc       432
Ala Glu Leu Lys Val Gln Ser Lys Pro Cys Thr Thr Ser Lys Glu Ile
130                 135                 140 gcc cag gta ggt tct atc tct gct aac tcc gac act tct gtt ggc caa       480
Ala Gln Val Gly Ser Ile Ser Ala Asn Ser Asp Thr Ser Val Gly Gln
145                 150                 155                 160 att att gct gat gcg atg gac aaa gta ggt aaa gaa ggc gtg atc act       528
Ile Ile Ala Asp Ala Met Asp Lys Val Gly Lys Glu Gly Val Ile Thr
                165                 170                 175 gtt gaa gac ggt tct ggc ttg agc aac gag ctg gac gtg gtt gag ggt       576
Val Glu Asp Gly Ser Gly Leu Ser Asn Glu Leu Asp Val Val Glu Gly
            180                 185                 190 atg caa ttt gat cgc ggt tac ttg tcc cca tac ttc atc aac aac cca       624
Met Gln Phe Asp Arg Gly Tyr Leu Ser Pro Tyr Phe Ile Asn Asn Pro
        195                 200                 205 gag cgc caa att gcg ttg ctg gac aat cct ttt gta ttg ttg cac gac       672
Glu Arg Gln Ile Ala Leu Leu Asp Asn Pro Phe Val Leu Leu His Asp
    210                 215                 220 aag aaa atc tcc aac atc cgt gac ctg ctg cca acc ctg gag caa gtg       720
Lys Lys Ile Ser Asn Ile Arg Asp Leu Leu Pro Thr Leu Glu Gln Val
225                 230                 235                 240 gct aaa gcc ggc cgt cca ttg ctg atc atc gct gaa gat gta gat ggc       768
Ala Lys Ala Gly Arg Pro Leu Leu Ile Ile Ala Glu Asp Val Asp Gly
                245                 250                 255 gaa gct ctg gca acg ttg gta gta aac aac atc cgc ggc atc ctg aaa       816
Glu Ala Leu Ala Thr Leu Val Val Asn Asn Ile Arg Gly Ile Leu Lys
            260                 265                 270 aca acc gct gtg aaa gcg cct ggt ttt ggt gac cgt cgt aaa gcg atg       864
Thr Thr Ala Val Lys Ala Pro Gly Phe Gly Asp Arg Arg Lys Ala Met
        275                 280                 285 ttg gaa gat atc gct gtg ctg acc ggt ggt acc gtg att tct gaa gaa       912
Leu Glu Asp Ile Ala Val Leu Thr Gly Gly Thr Val Ile Ser Glu Glu
    290                 295                 300 gtg ggc ctg aaa ctg gaa ggc gta cag ctg cac gac ctg ggt caa gcc       960
Val Gly Leu Lys Leu Glu Gly Val Gln Leu His Asp Leu Gly Gln Ala
305                 310                 315                 320 aaa cgt atc gaa gtg ggt aaa gaa aac acc atc atc att gat ggc gct      1008
Lys Arg Ile Glu Val Gly Lys Glu Asn Thr Ile Ile Ile Asp Gly Ala
                325                 330                 335 ggt aac gaa gaa gcg atc aaa gcg cgt atc ggc cag atc aaa acc caa      1056
Gly Asn Glu Glu Ala Ile Lys Ala Arg Ile Gly Gln Ile Lys Thr Gln
            340                 345                 350 atc gaa gaa gct tcc agc gac tac gac cgt gaa aaa ctg caa gag cgc      1104
```

-continued

```
Ile Glu Glu Ala Ser Ser Asp Tyr Asp Arg Glu Lys Leu Gln Glu Arg
            355                 360                 365 gtg gcc aaa ctg gct ggt ggt gtt gca gtg atc aag gtg ggt gct gcg      1152
Val Ala Lys Leu Ala Gly Gly Val Ala Val Ile Lys Val Gly Ala Ala
    370                 375                 380 act gag gtt gaa atg aaa gag aaa aaa gca cgc gtt gaa gat gca ttg      1200
Thr Glu Val Glu Met Lys Glu Lys Lys Ala Arg Val Glu Asp Ala Leu
385                 390                 395                 400 cac gcg act cgc gct gcg gtt gaa gaa ggt atc gtg gcg ggt ggt ggt      1248
His Ala Thr Arg Ala Ala Val Glu Glu Gly Ile Val Ala Gly Gly Gly
                405                 410                 415 gtt gca ttg atc cgt gct cgt gac gcg att gct aaa gtc aaa ggc gaa      1296
Val Ala Leu Ile Arg Ala Arg Asp Ala Ile Ala Lys Val Lys Gly Glu
            420                 425                 430 aac gct gat cag gat gct ggt atc aag atc gtt ctg cgt gcg gtt gaa      1344
Asn Ala Asp Gln Asp Ala Gly Ile Lys Ile Val Leu Arg Ala Val Glu
        435                 440                 445 gaa cca ctg cgc cag atc gtt tct aac gcc ggt gct gaa cca tct gtg      1392
Glu Pro Leu Arg Gln Ile Val Ser Asn Ala Gly Ala Glu Pro Ser Val
    450                 455                 460 gtt gtc agc aac gtt gct gct ggt aaa ggt aac tac ggt tac aac gct      1440
Val Val Ser Asn Val Ala Ala Gly Lys Gly Asn Tyr Gly Tyr Asn Ala
465                 470                 475                 480 gcc aac gaa acc tat ggc gac atg gtt gaa atg ggc gta ctg gat cca      1488
Ala Asn Glu Thr Tyr Gly Asp Met Val Glu Met Gly Val Leu Asp Pro
                485                 490                 495 acc aaa gtg aca cgt tct gcc ttg act aac gca gct tct gtc gct ggc      1536
Thr Lys Val Thr Arg Ser Ala Leu Thr Asn Ala Ala Ser Val Ala Gly
            500                 505                 510 ctg atg ctg acg act gac tgc atg gtc gca gaa ctg cct aaa gaa gat      1584
Leu Met Leu Thr Thr Asp Cys Met Val Ala Glu Leu Pro Lys Glu Asp
        515                 520                 525 gca cct gct gcg ccg gat atg ggc ggg atg ggt ggc atg ggc ggt atg      1632
Ala Pro Ala Ala Pro Asp Met Gly Gly Met Gly Gly Met Gly Gly Met
    530                 535                 540 atg taa                                                              1638
Met
545

<210> SEQ ID NO 28
<211> LENGTH: 545
<212> TYPE: PRT
<213> ORGANISM: Methylophilus methylotrophus

<400> SEQUENCE: 28

Met Ala Ala Lys Asp Val Arg Phe Gly Asp Asp Val Arg Gln Lys Met
1               5                   10                  15

Val Asn Gly Val Asn Val Leu Ala Asn Ala Val Arg Val Thr Leu Gly
            20                  25                  30

Pro Lys Gly Arg Asn Val Val Leu Glu Arg Ser Phe Gly Ala Pro Thr
        35                  40                  45

Ile Thr Lys Asp Gly Val Ser Val Ala Lys Glu Ile Glu Leu Lys Asp
    50                  55                  60

Lys Phe Glu Asn Met Gly Ala Gln Met Val Lys Glu Val Ala Ser Lys
65                  70                  75                  80

Thr Asn Asp Ile Ala Gly Asp Gly Thr Thr Thr Ala Thr Val Leu Ala
                85                  90                  95

Gln Ala Ile Ile Arg Glu Gly Met Lys Ser Val Ala Ala Gly Met Asn
            100                 105                 110
```

-continued

```
Pro Met Asp Leu Lys Arg Gly Ile Asp Lys Ala Val Glu Ala Ala Ile
        115                 120                 125
Ala Glu Leu Lys Val Gln Ser Lys Pro Cys Thr Thr Ser Lys Glu Ile
    130                 135                 140
Ala Gln Val Gly Ser Ile Ser Ala Asn Ser Asp Thr Ser Val Gly Gln
145                 150                 155                 160
Ile Ile Ala Asp Ala Met Asp Lys Val Gly Lys Glu Gly Val Ile Thr
                165                 170                 175
Val Glu Asp Gly Ser Gly Leu Ser Asn Glu Leu Asp Val Val Glu Gly
            180                 185                 190
Met Gln Phe Asp Arg Gly Tyr Leu Ser Pro Tyr Phe Ile Asn Asn Pro
        195                 200                 205
Glu Arg Gln Ile Ala Leu Leu Asp Asn Pro Phe Val Leu Leu His Asp
    210                 215                 220
Lys Lys Ile Ser Asn Ile Arg Asp Leu Leu Pro Thr Leu Glu Gln Val
225                 230                 235                 240
Ala Lys Ala Gly Arg Pro Leu Leu Ile Ile Ala Glu Asp Val Asp Gly
                245                 250                 255
Glu Ala Leu Ala Thr Leu Val Val Asn Asn Ile Arg Gly Ile Leu Lys
            260                 265                 270
Thr Thr Ala Val Lys Ala Pro Gly Phe Gly Asp Arg Arg Lys Ala Met
        275                 280                 285
Leu Glu Asp Ile Ala Val Leu Thr Gly Gly Thr Val Ile Ser Glu Glu
    290                 295                 300
Val Gly Leu Lys Leu Glu Gly Val Gln Leu His Asp Leu Gly Gln Ala
305                 310                 315                 320
Lys Arg Ile Glu Val Gly Lys Glu Asn Thr Ile Ile Ile Asp Gly Ala
                325                 330                 335
Gly Asn Glu Glu Ala Ile Lys Ala Arg Ile Gly Gln Ile Lys Thr Gln
            340                 345                 350
Ile Glu Glu Ala Ser Ser Asp Tyr Asp Arg Glu Lys Leu Gln Glu Arg
        355                 360                 365
Val Ala Lys Leu Ala Gly Gly Val Ala Val Ile Lys Val Gly Ala Ala
    370                 375                 380
Thr Glu Val Glu Met Lys Glu Lys Lys Ala Arg Val Glu Asp Ala Leu
385                 390                 395                 400
His Ala Thr Arg Ala Ala Val Glu Glu Gly Ile Val Ala Gly Gly Gly
                405                 410                 415
Val Ala Leu Ile Arg Ala Arg Asp Ala Ile Ala Lys Val Lys Gly Glu
            420                 425                 430
Asn Ala Asp Gln Asp Ala Gly Ile Lys Ile Val Leu Arg Ala Val Glu
        435                 440                 445
Glu Pro Leu Arg Gln Ile Val Ser Asn Ala Gly Ala Glu Pro Ser Val
    450                 455                 460
Val Val Ser Asn Val Ala Ala Gly Lys Gly Asn Tyr Gly Tyr Asn Ala
465                 470                 475                 480
Ala Asn Glu Thr Tyr Gly Asp Met Val Glu Met Gly Val Leu Asp Pro
                485                 490                 495
Thr Lys Val Thr Arg Ser Ala Leu Thr Asn Ala Ala Ser Val Ala Gly
            500                 505                 510
Leu Met Leu Thr Thr Asp Cys Met Val Ala Glu Leu Pro Lys Glu Asp
        515                 520                 525
```

```
            Ala Pro Ala Ala Pro Asp Met Gly Gly Met Gly Gly Met
                530                 535                 540

Met
545

<210> SEQ ID NO 29
<211> LENGTH: 288
<212> TYPE: DNA
<213> ORGANISM: Methylophilus methylotrophus
<220> FEATURE:
<221> NAME/KEY: CDS
<222> LOCATION: (1)..(288)
<223> OTHER INFORMATION:

<400> SEQUENCE: 29 atg aac att cgt ccg ttg cac gac cgt gta att gtt aaa cgc gct gct      48
Met Asn Ile Arg Pro Leu His Asp Arg Val Ile Val Lys Arg Ala Ala
  1               5                  10                  15 gaa gag cgc acc act gct tct ggc att gtg atc cct gac agt gcg act      96
Glu Glu Arg Thr Thr Ala Ser Gly Ile Val Ile Pro Asp Ser Ala Thr
             20                  25                  30 gag aaa cca gat caa ggt gtg gtt cag gca gtt ggc aat ggc aaa aaa     144
Glu Lys Pro Asp Gln Gly Val Val Gln Ala Val Gly Asn Gly Lys Lys
         35                  40                  45 gat gaa aac ggc aaa gca att gcc ttg gac gtg aaa gtc ggc gac aag     192
Asp Glu Asn Gly Lys Ala Ile Ala Leu Asp Val Lys Val Gly Asp Lys
     50                  55                  60 gta ttg ttc ggc aaa tac tcc ggt caa aca gtg aaa gtc aac ggc gaa     240
Val Leu Phe Gly Lys Tyr Ser Gly Gln Thr Val Lys Val Asn Gly Glu
 65                  70                  75                  80 gag ctg ttg gtg atg cgc gaa gaa gac att atg gcg att gtt gag taa     288
Glu Leu Leu Val Met Arg Glu Glu Asp Ile Met Ala Ile Val Glu
                 85                  90                  95

<210> SEQ ID NO 30
<211> LENGTH: 95
<212> TYPE: PRT
<213> ORGANISM: Methylophilus methylotrophus

<400> SEQUENCE: 30

Met Asn Ile Arg Pro Leu His Asp Arg Val Ile Val Lys Arg Ala Ala
  1               5                  10                  15

Glu Glu Arg Thr Thr Ala Ser Gly Ile Val Ile Pro Asp Ser Ala Thr
             20                  25                  30

Glu Lys Pro Asp Gln Gly Val Val Gln Ala Val Gly Asn Gly Lys Lys
         35                  40                  45

Asp Glu Asn Gly Lys Ala Ile Ala Leu Asp Val Lys Val Gly Asp Lys
     50                  55                  60

Val Leu Phe Gly Lys Tyr Ser Gly Gln Thr Val Lys Val Asn Gly Glu
 65                  70                  75                  80

Glu Leu Leu Val Met Arg Glu Glu Asp Ile Met Ala Ile Val Glu
                 85                  90                  95

<210> SEQ ID NO 31
<211> LENGTH: 1620
<212> TYPE: DNA
<213> ORGANISM: Methylophilus methylotrophus
<220> FEATURE:
<221> NAME/KEY: CDS
<222> LOCATION: (1)..(1620)
<223> OTHER INFORMATION:

<400> SEQUENCE: 31
```

```
atg gca gca aaa gat gtg aaa ttt cat gat cat gcg cgc act aaa att      48
Met Ala Ala Lys Asp Val Lys Phe His Asp His Ala Arg Thr Lys Ile
1               5                  10                 15 gta aaa ggc gtg aat atc ctg gcc gat gcg gtc aag gtt acc ttg ggg      96
Val Lys Gly Val Asn Ile Leu Ala Asp Ala Val Lys Val Thr Leu Gly
            20                 25                 30 ccc aaa ggc cgt aat gtc gtg ctg gag cgc agc ttt ggc gcc ccg gtg     144
Pro Lys Gly Arg Asn Val Val Leu Glu Arg Ser Phe Gly Ala Pro Val
        35                 40                 45 att acc aaa gat ggt gtc tcc gtt gcc aag gaa atc gag ttg cag gac     192
Ile Thr Lys Asp Gly Val Ser Val Ala Lys Glu Ile Glu Leu Gln Asp
    50                 55                 60 aag ctg gag aat atg ggc gca caa atg gtg aag caa gtc gct tct aaa     240
Lys Leu Glu Asn Met Gly Ala Gln Met Val Lys Gln Val Ala Ser Lys
65                 70                 75                 80 aca gct gac gtg gcc ggt gac ggt acg act acc gct acc gtg ctg gct     288
Thr Ala Asp Val Ala Gly Asp Gly Thr Thr Thr Ala Thr Val Leu Ala
                85                 90                 95 cag gcg att gta caa gaa ggg atg aag tca gtc gcc tcc ggc atg aat     336
Gln Ala Ile Val Gln Glu Gly Met Lys Ser Val Ala Ser Gly Met Asn
            100                105                110 ccc acc gac cta aaa cgt ggg att gat aaa gcc gtg aca gcc ctg gtg     384
Pro Thr Asp Leu Lys Arg Gly Ile Asp Lys Ala Val Thr Ala Leu Val
        115                120                125 gat gag ctt aaa tcc atg tcc aaa gct atc acc acc cat aaa gaa att     432
Asp Glu Leu Lys Ser Met Ser Lys Ala Ile Thr Thr His Lys Glu Ile
    130                135                140 gcc caa gtc ggt gcg att tct gcc aac tct gac cat gcc att ggc cag     480
Ala Gln Val Gly Ala Ile Ser Ala Asn Ser Asp His Ala Ile Gly Gln
145                150                155                160 atc atc gcc gat gcc atg gaa aaa gtc ggt aaa gaa ggc gtg att acg     528
Ile Ile Ala Asp Ala Met Glu Lys Val Gly Lys Glu Gly Val Ile Thr
                165                170                175 gtg gaa gaa ggt aag tca ctg caa aat gaa ctc gaa gtg gtc gag ggc     576
Val Glu Glu Gly Lys Ser Leu Gln Asn Glu Leu Glu Val Val Glu Gly
            180                185                190 atg cag ttt gac cgc ggc tat atc agc ccc tac ttt att aac aac cct     624
Met Gln Phe Asp Arg Gly Tyr Ile Ser Pro Tyr Phe Ile Asn Asn Pro
        195                200                205 gac aag cag gta gca gct ctc gat gag ccc atg att ctg ctt tac gac     672
Asp Lys Gln Val Ala Ala Leu Asp Glu Pro Met Ile Leu Leu Tyr Asp
    210                215                220 aaa aaa atc agc aat atc cgt gac ttg ttg cca acc ctg gaa aac gtc     720
Lys Lys Ile Ser Asn Ile Arg Asp Leu Leu Pro Thr Leu Glu Asn Val
225                230                235                240 gcc aag gcc aac aaa ccc ttg ctg atc att gcc gaa gac gtg gag ggc     768
Ala Lys Ala Asn Lys Pro Leu Leu Ile Ile Ala Glu Asp Val Glu Gly
                245                250                255 gaa gcc ctg gcc acc ctg gtg gtc aat agc atg cgc ggt atc ctc aaa     816
Glu Ala Leu Ala Thr Leu Val Val Asn Ser Met Arg Gly Ile Leu Lys
            260                265                270 gtg gtt gct gtg aaa gca cct ggc ttt ggt gac cgc cgc aaa gcc atg     864
Val Val Ala Val Lys Ala Pro Gly Phe Gly Asp Arg Arg Lys Ala Met
        275                280                285 ctg gaa gac att gcc gtc ctg acc ggg gcc act gtg gtt tcc gaa gaa     912
Leu Glu Asp Ile Ala Val Leu Thr Gly Ala Thr Val Val Ser Glu Glu
    290                295                300 acc ggc atg caa ctg gaa aaa gtg act ctt gaa cac ttg ggc cac gcc     960
Thr Gly Met Gln Leu Glu Lys Val Thr Leu Glu His Leu Gly His Ala
```

-continued

```
                305                 310                 315                 320
aag cgc gtt gaa gtg caa aaa gag aat acc atc att att gat ggc gca        1008
Lys Arg Val Glu Val Gln Lys Glu Asn Thr Ile Ile Ile Asp Gly Ala
                325                 330                 335 ggt gat gca gcc aag att aag gcc cgc gtg cag tcc atc cgg act caa        1056
Gly Asp Ala Ala Lys Ile Lys Ala Arg Val Gln Ser Ile Arg Thr Gln
            340                 345                 350 ata gag gaa gcc acc tct gat tat gac aag gaa aaa ctg cag gag cgc        1104
Ile Glu Glu Ala Thr Ser Asp Tyr Asp Lys Glu Lys Leu Gln Glu Arg
        355                 360                 365 gtg gcc aaa ctg ggt ggt ggc gtg gcg gtg att aaa atc ggc gcc gcg        1152
Val Ala Lys Leu Gly Gly Gly Val Ala Val Ile Lys Ile Gly Ala Ala
    370                 375                 380 acc gaa gtc gaa atg aaa gag aaa aaa gac cgt gtc gat gat gct cta        1200
Thr Glu Val Glu Met Lys Glu Lys Lys Asp Arg Val Asp Asp Ala Leu
385                 390                 395                 400 cac gcc aca cgg gct gcg gtg gaa gaa ggc atc gtt cca ggt ggc ggt        1248
His Ala Thr Arg Ala Ala Val Glu Glu Gly Ile Val Pro Gly Gly Gly
                405                 410                 415 gtg gct ctg ctg cgt gcc cgc agc cgc atg agc act ctc aag ggc gat        1296
Val Ala Leu Leu Arg Ala Arg Ser Arg Met Ser Thr Leu Lys Gly Asp
            420                 425                 430 aat gat gac cag gaa gcc ggt atc cgc att gtg ttg cgt gca ata gaa        1344
Asn Asp Asp Gln Glu Ala Gly Ile Arg Ile Val Leu Arg Ala Ile Glu
        435                 440                 445 gag ccc tta cgc gcg att gtg aaa aat gca ggt gaa gag cct tct gtc        1392
Glu Pro Leu Arg Ala Ile Val Lys Asn Ala Gly Glu Glu Pro Ser Val
    450                 455                 460 gtc atc gcc aag gtg ctt gag gca aca ggt aat acc ggc tac aac gca        1440
Val Ile Ala Lys Val Leu Glu Ala Thr Gly Asn Thr Gly Tyr Asn Ala
465                 470                 475                 480 gcc acc ggt gaa tat gtg gat atg gtg gaa acc ggt gtg gtg gac cca        1488
Ala Thr Gly Glu Tyr Val Asp Met Val Glu Thr Gly Val Val Asp Pro
                485                 490                 495 acc aag gtg acc cgc act gcc ctg caa aat gca gcc tcg att gcc ggt        1536
Thr Lys Val Thr Arg Thr Ala Leu Gln Asn Ala Ala Ser Ile Ala Gly
            500                 505                 510 ctg att tta acc acc gac gcc acc gtg gct gaa cta ccc aaa gag gag        1584
Leu Ile Leu Thr Thr Asp Ala Thr Val Ala Glu Leu Pro Lys Glu Glu
        515                 520                 525 aaa aag gcg cca gcc atg cca gaa atg gag tac taa                        1620
Lys Lys Ala Pro Ala Met Pro Glu Met Glu Tyr
    530                 535

<210> SEQ ID NO 32
<211> LENGTH: 539
<212> TYPE: PRT
<213> ORGANISM: Methylophilus methylotrophus

<400> SEQUENCE: 32

Met Ala Ala Lys Asp Val Lys Phe His Asp His Ala Arg Thr Lys Ile
1               5                   10                  15

Val Lys Gly Val Asn Ile Leu Ala Asp Ala Val Lys Val Thr Leu Gly
            20                  25                  30

Pro Lys Gly Arg Asn Val Val Leu Glu Arg Ser Phe Gly Ala Pro Val
        35                  40                  45

Ile Thr Lys Asp Gly Val Ser Val Ala Lys Glu Ile Glu Leu Gln Asp
    50                  55                  60

Lys Leu Glu Asn Met Gly Ala Gln Met Val Lys Gln Val Ala Ser Lys
```

```
            65                  70                  75                  80
Thr Ala Asp Val Ala Gly Asp Gly Thr Thr Thr Ala Thr Val Leu Ala
                    85                  90                  95
Gln Ala Ile Val Gln Glu Gly Met Lys Ser Val Ala Ser Gly Met Asn
                    100                 105                 110
Pro Thr Asp Leu Lys Arg Gly Ile Asp Lys Ala Val Thr Ala Leu Val
                    115                 120                 125
Asp Glu Leu Lys Ser Met Ser Lys Ala Ile Thr Thr His Lys Glu Ile
                    130                 135                 140
Ala Gln Val Gly Ala Ile Ser Ala Asn Ser Asp His Ala Ile Gly Gln
145                 150                 155                 160
Ile Ile Ala Asp Ala Met Glu Lys Val Gly Lys Glu Gly Val Ile Thr
                    165                 170                 175
Val Glu Glu Gly Lys Ser Leu Gln Asn Glu Leu Glu Val Val Glu Gly
                    180                 185                 190
Met Gln Phe Asp Arg Gly Tyr Ile Ser Pro Tyr Phe Ile Asn Asn Pro
                    195                 200                 205
Asp Lys Gln Val Ala Ala Leu Asp Glu Pro Met Ile Leu Leu Tyr Asp
                    210                 215                 220
Lys Lys Ile Ser Asn Ile Arg Asp Leu Leu Pro Thr Leu Glu Asn Val
225                 230                 235                 240
Ala Lys Ala Asn Lys Pro Leu Leu Ile Ile Ala Glu Asp Val Glu Gly
                    245                 250                 255
Glu Ala Leu Ala Thr Leu Val Val Asn Ser Met Arg Gly Ile Leu Lys
                    260                 265                 270
Val Val Ala Val Lys Ala Pro Gly Phe Gly Asp Arg Arg Lys Ala Met
                    275                 280                 285
Leu Glu Asp Ile Ala Val Leu Thr Gly Ala Thr Val Val Ser Glu Glu
                    290                 295                 300
Thr Gly Met Gln Leu Glu Lys Val Thr Leu Glu His Leu Gly His Ala
305                 310                 315                 320
Lys Arg Val Glu Val Gln Lys Glu Asn Thr Ile Ile Ile Asp Gly Ala
                    325                 330                 335
Gly Asp Ala Ala Lys Ile Lys Ala Arg Val Gln Ser Ile Arg Thr Gln
                    340                 345                 350
Ile Glu Glu Ala Thr Ser Asp Tyr Asp Lys Glu Lys Leu Gln Glu Arg
                    355                 360                 365
Val Ala Lys Leu Gly Gly Gly Val Ala Val Ile Lys Ile Gly Ala Ala
                    370                 375                 380
Thr Glu Val Glu Met Lys Glu Lys Lys Asp Arg Val Asp Asp Ala Leu
385                 390                 395                 400
His Ala Thr Arg Ala Ala Val Glu Glu Gly Ile Val Pro Gly Gly Gly
                    405                 410                 415
Val Ala Leu Leu Arg Ala Arg Ser Arg Met Ser Thr Leu Lys Gly Asp
                    420                 425                 430
Asn Asp Asp Gln Glu Ala Gly Ile Arg Ile Val Leu Arg Ala Ile Glu
                    435                 440                 445
Glu Pro Leu Arg Ala Ile Val Lys Asn Ala Gly Glu Glu Pro Ser Val
                    450                 455                 460
Val Ile Ala Lys Val Leu Glu Ala Thr Gly Asn Thr Gly Tyr Asn Ala
465                 470                 475                 480
Ala Thr Gly Glu Tyr Val Asp Met Val Glu Thr Gly Val Val Asp Pro
                    485                 490                 495
```

```
Thr Lys Val Thr Arg Thr Ala Leu Gln Asn Ala Ala Ser Ile Ala Gly
        500                 505                 510

Leu Ile Leu Thr Thr Asp Ala Thr Val Ala Glu Leu Pro Lys Glu Glu
        515                 520                 525

Lys Lys Ala Pro Ala Met Pro Glu Met Glu Tyr
        530                 535

<210> SEQ ID NO 33
<211> LENGTH: 318
<212> TYPE: DNA
<213> ORGANISM: Methylophilus methylotrophus
<220> FEATURE:
<221> NAME/KEY: CDS
<222> LOCATION: (1)..(318)
<223> OTHER INFORMATION:

<400> SEQUENCE: 33 atg aat att cgt ccc ctg tat gac cgc gtc att gtc aag cga gtc gag      48
Met Asn Ile Arg Pro Leu Tyr Asp Arg Val Ile Val Lys Arg Val Glu
1               5                  10                  15 caa caa cgg acg acc gct tcc ggc att gtg atc cct gac act gca gca      96
Gln Gln Arg Thr Thr Ala Ser Gly Ile Val Ile Pro Asp Thr Ala Ala
            20                  25                  30 gaa aag cca gag caa gga gag gtc att gcc gtg ggc agt ggc aaa cag     144
Glu Lys Pro Glu Gln Gly Glu Val Ile Ala Val Gly Ser Gly Lys Gln
        35                  40                  45 ctg cag gac ggt agc ctg cga cca ctg gaa gtc aag gtg ggc aac cat     192
Leu Gln Asp Gly Ser Leu Arg Pro Leu Glu Val Lys Val Gly Asn His
    50                  55                  60 atc ctg ttt ggc aag tat tct ggt caa acg gtc aag ctt aac ggc gag     240
Ile Leu Phe Gly Lys Tyr Ser Gly Gln Thr Val Lys Leu Asn Gly Glu
65                  70                  75                  80 gaa ctg ctg gtc atg cgt gag gaa gac att ctc ggc gtg att gaa ccc     288
Glu Leu Leu Val Met Arg Glu Glu Asp Ile Leu Gly Val Ile Glu Pro
                85                  90                  95 agt cct gcc gac ctc aaa aaa gtc gct taa                             318
Ser Pro Ala Asp Leu Lys Lys Val Ala
                100                 105

<210> SEQ ID NO 34
<211> LENGTH: 105
<212> TYPE: PRT
<213> ORGANISM: Methylophilus methylotrophus

<400> SEQUENCE: 34

Met Asn Ile Arg Pro Leu Tyr Asp Arg Val Ile Val Lys Arg Val Glu
1               5                  10                  15

Gln Gln Arg Thr Thr Ala Ser Gly Ile Val Ile Pro Asp Thr Ala Ala
            20                  25                  30

Glu Lys Pro Glu Gln Gly Glu Val Ile Ala Val Gly Ser Gly Lys Gln
        35                  40                  45

Leu Gln Asp Gly Ser Leu Arg Pro Leu Glu Val Lys Val Gly Asn His
    50                  55                  60

Ile Leu Phe Gly Lys Tyr Ser Gly Gln Thr Val Lys Leu Asn Gly Glu
65                  70                  75                  80

Glu Leu Leu Val Met Arg Glu Glu Asp Ile Leu Gly Val Ile Glu Pro
                85                  90                  95

Ser Pro Ala Asp Leu Lys Lys Val Ala
                100                 105
```

POLYNUCLEOTIDES ENCODING POLYPEPTIDES INVOLVED IN THE STRESS RESPONSE TO ENVIRONMENTAL CHANGES IN *METHYLOPHILUS METHYLOTROPHUS*

BACKGROUND OF THE INVENTION

1. Field of the Invention

The present invention relates to novel polynucleotides encoding proteins involved in the stress response to environmental changes including DNA damages, phage infection and physiological stresses, derived from microorganisms belonging to methylotrophic bacteria and fragments thereof, polypeptides encoded by the polynucleotides and fragments thereof, polynucleotide arrays comprising the polynucleotides and fragments thereof.

2. Discussion of the Background

Amino acids such as L-lysine, L-glutamic acid, L-threonine, L-leucine, L-isoleucine, L-valine and L-phenylalanine are industrially produced by fermentation by using microorganisms that belong to the genus *Brevibacterium, Corynebacterium, Bacillus, Escherichia, Streptomyces, Pseudomonas, Arthrobacter, Serratia, Penicillium, Candida* or the like. In order to improve the productivity of amino acids, strains of the aforementioned microorganisms that have been isolated from nature or artificial mutants thereof have been used. Various techniques have also been disclosed for enhancing activities of L-amino acid biosynthetic enzymes by using recombinant DNA techniques to increase the L-amino acid-producing ability.

L-amino acid production has been increased considerably by breeding of microorganisms such as those mentioned above and by improvements in production methods. However, in order to meet a future increase in the demand for L-amino acids, development of methods for more efficiently producing L-amino acids at lower cost are still desired.

Conventional methods for producing amino acids by fermentation using methanol, which is a raw fermentation material available in large quantities at a low cost, employ Achromobacter or *Pseudomonas* microorganisms (Japanese Patent Publication (Kokoku) No. 45-25273/1970), *Protaminobacter* microorganisms (Japanese Patent Application Laid-open (Kokai) No. 49-125590/1974), *Protaminobacter* or *Methanomonas* microorganisms (Japanese Patent Application Laid-open (Kokai) No. 50-25790/1975), *Microcyclus* microorganisms (Japanese Patent Application Laid-open (Kokai) No. 52-18886/1977), *Methylobacillus* microorganisms (Japanese Patent Application Laid-open (Kokai) No. 4-91793/1992), Bacillus microorganisms (Japanese Patent Application Laid-open (Kokai) No. 3-505284/1991) and others.

However, only a few methods have been described for producing L-amino acids using *Methylophilus* bacteria in conjunction with recombinant DNA technology. Although methods described in EP 0 035 831 A, EP 0 037 273 A and EP 0 066 994 A have been described as methods for transforming *Methylophilus* bacteria using recombinant DNA, applying recombinant DNA techniques to improvement of amino acid productivity of *Methylophilus* bacteria has not been described. Only WO-00/61723 and WO-02/38777 disclose the improved production of lysine and phenylalanine, respectively, using genes involved in biosynthesis of each respective amino acid. In particular, WO-00/61723 discloses the ask gene, the dapA gene, the dapB gene, and the lysA gene, which encode aspartkinase, dihydrodipicolinate synthase, dihydrodipicolinate reductase, and diaminopimelinate decarboxylase, respectively. WO-02/38777 discloses the aroG gene and the pheA gene, which encode 3-deoxy-D-arabino-heptulosonate 7-phosphate synthase and bi-functional enzyme of chorismate mutase and prephenate dehydratase, respectively.

Therefore, prior to the present invention genes isolated from *Methylophilus* bacteria that are involved in the stress response to environmental changes and which can be used to improve the yield of amino acids in cultured microorganisms remain elusive and undisclosed.

SUMMARY OF THE INVENTION

An object of the present invention is to provide novel measures for the improved production of amino acids or an amino acid, where these amino acids include asparagine, threonine, serine, glutamate, glycine, alanine, cysteine, valine, methionine, isoleucine, leucine, tyrosine, phenylalanine, histidine, lysine, tryptophan, arginine and the salts thereof. In a preferred embodiment the amino acids are L-amino acids.

Such a process includes bacteria, which express a protein comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34.

In one embodiment the polypeptides are encoded by a polynucleotide selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33. In another embodiment the polypeptides are encoded by other polynucleotides which have substantial identity to the herein described polynucleotides or those which hybridize under stringent conditions.

Another object of the invention is to provide polynucleotide sequences selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33; as well as those polynucleotides that have substantial identity to these nucleotide sequences, preferably at least 95% identity.

Another object of the invention is to provide isolated polypeptides having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34; as well as those polypeptides that have substantial identity to these amino acid sequences, preferably at least 95% identity.

A further object of the invention is a method for producing a protein or proteins by culturing host cells containing the herein described polynucleotides under conditions and for a time suitable for expression of the protein and collecting the protein produced thereby.

Another object is the use of host cells having the polynucleotides described herein to produce amino acids, as well as the use of such isolated polypeptides in the production of amino acids.

Other objects of the invention include methods of detecting nucleic acid sequences homologous to at least one of:

SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, particularly nucleic acid sequences encoding polypeptides that herein described proteins or polypeptides and methods of making nucleic acids encoding such polypeptides.

The above objects highlight certain aspects of the invention. Additional objects, aspects and embodiments of the invention are found in the following detailed description of the invention.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausebel et al (eds.), John Wiley & Sons, New York (2001) and the various references cited therein.

*Methylophilus methylotrophus* (*M. methylotrophus*) is a gram negative ribulose monophosphate cycle methanol-utilizer, which can be used for the large-scale production of a variety of fine chemicals including amino acids, nucleic acids, vitamins, saccharides, and so on. The polynucleotides of this invention, therefore, can be used to identify microorganisms, which can be used to produce fine chemicals, for example, by fermentative processes. Modulation of the expression of the polynucleotides encoding proteins in the stress response to environmental changes of the present invention, can be used to modulate the production of one or more fine chemicals from a microorganism (e.g., to improve the yield of production of one or more fine chemicals from *Methylophilus* or *Methylbacillus* species).

The proteins encoded by the polynucleotides of the present invention are capable of, for example, performing a function involved in the stress response to environmental changes in *M. methylotrophus*, such as, DNA damages, phage infection and several physiological stresses.

Given the availability of cloning vectors used in *M. methylotrophus*, such as those disclosed in Methane and Methanol Utilizers, Plenum Press, New York (1992) edited by J. Colin Murrell and Howard Dalton, the nucleic acid molecules of the present invention may be used in the genetic engineering of this organism to make it better or more efficient producer of one or more fine chemicals.

There are a number of mechanisms by which the alteration of a protein of the present invention may affect the yield, production, and/or efficiency of production of a fine chemical from *M. methylotrophus* bacteria, which have the altered protein incorporated.

Improving the ability of the cell to produce integration host factors (e.g., by manipulating the genes expression or the efficiency of translation of the mRNAs), one could efficiently transfer transposon, such as Mu-phage, in the host cell in order to amplify the desired gene-cassette on the chromosome using this phage-function. For example, one can place the important genes for amino acid synthesis onto the gene-cassette, and the efficiency of the transposition or amplification of the gene-cassette derived from transposon, such as Mu-phage, could be increased by the function of integration host factors. In addition, several recombinant proteins, RecR, RecN, and RecO, could facilitate the reactions. The rapid DNA manipulation may save the cost associated with breeding of the microorganism during the production of the desired fine-chemicals. On the other hand, the inactivations of these genes might give the host cells the tolerance to some bacterial phages. The property may be advantageous for large-scale fermentation of the microorganism during the production of the desired fine-chemicals.

Improving the ability of the cell to tolerate some stresses could increase the yield or productivity of desired fine chemicals, since the disturbed physiological conditions for the over-production may induce mutations in the producer cells resulting in low-productivity. Therefore, the improvement of stress tolerance may be favorable to the microorganism for the over-production of the desired fine-chemicals, and may allow the microorganism to sustain high-level productivity. Those candidate genes are RNA polymerase sigma factor D (rpoD), RNA polymerase sigma factor E (rpoE), RNA polymerase sigma factor H (rpoH), RNA polymerase sigma factor N (rpoN), Chaperone protein DnaK (dnaK), Chaperone protein DnaJ (dnaJ), Chaperone protein HscA (hscA), Chaperone protein HscB (hscB), Chaperone protein GroEL1 (groEL1), Chaperone protein GroES1 (groES1), Chaperone protein GroEL2 (groEL2), and Chaperone protein GroES2 (groES2).

"L-amino acids" or "amino acids" as used herein means one or more amino acids, including their salts, preferably chosen from the following: L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine.

"Isolated" as used herein means separated out of its natural environment.

"Substantial identity" as used herein refers to polynucleotides and polypeptides which are at least 70%, preferably at least 80% and more preferably at least 90% to 95% identical to the polynucleotides and polypeptides, respectively, according to the present invention.

"Polynucleotide" as used herein relates to polyribonucleotides and polydeoxyribonucleotides, it being possible for these to be non-modified RNA or DNA or modified RNA or DNA.

"Polypeptides" as used herein are understood to mean peptides or proteins which comprise two or more amino acids bonded via peptide bonds. In particular, the term refers to polypeptides which are at least 70%, preferably at least 80% and more preferably at least 90% to 95% identical to the polypeptides according to the present invention. Included within the scope of the present invention are polypeptide fragments of the polypeptides having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34 or those which are identical to those described herein.

"Polynucleotides which encode the polypeptide" of the invention as used herein is understood to mean the sequences exemplified in this application as well as those sequences which have substantial identity to the nucleic acid sequences at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33 and which encode a molecule having one or more of the bioactivities of the associated gene products. Preferably, such polynucleotides are those which are at least 70%, preferably at least 80% and more preferably at least 90% to 95% identical to the nucleic acid sequences at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33.

Polynucleotides according to the invention may be employed as probes to isolate and/or identify RNA, cDNA and DNA molecules, e.g., full-length genes or polynucleotides which code for the polypeptides described herein. Likewise, the probes can be employed to isolate nucleic acids, polynucleotides or genes which have a high sequence similarity or identity with the polynucleotides of the invention.

Polynucleotides of the invention may also be used to design primers useful for the polymerase chain reaction to amplify, identify and/or isolate full-length DNA, RNA or other polynucleotides with high sequence homology or identity to the polynucleotides of the invention, as well as, polynucleotides that encode the polypeptides of the invention.

Preferably, probes or primers are at least 15, 16, 17, 18, 19, 20, 21, 22, 23, 24, 25, 26, 27, 28, 29 or 30 nucleotides in length. Oligonucleotides with a length of at least 35, 40, 45, 50, 100, 150, 200, 250 or 300 nucleotides may also be used.

Methods of DNA sequencing are described inter alia by Sanger et al. (Proceedings of the National Academy of Sciences of the United States of America USA, 74:5463–5467, (1977)).

A person skilled in the art will find instructions for amplification of DNA sequences with the aid of the polymerase chain reaction (PCR) inter alia in the handbook by Gait: Oligonucleotide Synthesis: A Practical Approach (IRL Press, Oxford, UK, 1984) and in Newton and Graham: PCR $2^{nd}$ Edition (Springer Verlag, New York, 1997).

Additionally, methods employing DNA chips, microarrays or similar recombinant DNA technology that enables high throughput screening of DNA and polynucleotides that encode the herein described proteins or polynucleotides with high sequence homology or identity to the polynucleotides described herein. Such methods are known in the art and are described, for example, in Current Protocols in Molecular Biology, Ausebel et al (eds), John Wiley and Sons, Inc. New York (2000).

The polynucleotides and polypeptides of the present invention are involved in the stress response to environmental changes in *M. methylotrophus*. By way of example, the present inventors provide the following cited references (each of which are incorporated herein by reference) demonstrating that assays to assess the enzymatic activity of the polypeptides of the present invention are known and, as such, determination of whether a sequence falls within the scope of the present claims may be readily ascertained. These polynucleotides and polypeptides include:

1. Recombinant protein RecR comprises the amino acid sequence of SEQ ID NO:2 and is encoded by the recR gene which comprises the polynucleotide SEQ ID NO:1 (According to Pelaez, A. I. et. al. Mol. Gen. Genet. (2001) 265:663–672, the recR deficient mutant is more sensitive to DNA damage caused by UV irradiation or meythylmethane sulfonate than the wild type);

2. Recombinant protein RecN comprises the amino acid sequence of SEQ ID NO:4 and is encoded by the recN gene which comprises the polynucleotide SEQ ID NO:3 (The recN disruption mutant shows sensitivity to mitomycin C and ionizing radiation (Picksley, S. M. et. al. Mol. Gen. Genet. (1984) 195:267–274));

3. Recombinant protein RecO comprises the amino acid sequence of SEQ ID NO:6 and is encoded by the recO gene which comprises the polynucleotide SEQ ID NO:5 (The RecO activity can be measured as described by Luisi-DeLuca, C. and Kolodner, R (J. Mol. Biol. (1994) 236:124–138));

4. Integration host factor alpha-subunit enzyme comprises the amino acid sequence of SEQ ID NO:8 and is encoded by the infA gene which comprises the polynucleotide SEQ ID NO:7 (The activity of integration host factor can be measured through complementation of *E. coli* ifhA and ihjB mutant (Club, R. et. al., J. Bacteriol. (1996) 178: 6319–6326));

5. Integration host factor beta-subunit enzyme comprises the amino acid sequence of SEQ ID NO:10 and is encoded by a infB gene which comprises the polynucleotide SEQ ID NO:9 (The activity of integration host factor can be measured through complementation of *E. coli* ifhA and ihfB mutant (Club, R. et. al., J. Bacteriol. (1996) 178: 6319–6326));

6. RNA polymerase sigma factor D comprises the amino acid sequence of SEQ ID NO:12 and is encoded by a rpoD gene which comprises the polynucleotide SEQ ID NO:11 (The activity of RpoD can be assayed in combination with DNA dependent RNA polymerase core enzyme (Gribskov, M. and Burgess, R. R. Gene (1983) 26:109–118));

7. RNA polymerase sigma factor E comprises the amino acid sequence of SEQ ID NO:14 and is encoded by a rpoE gene which comprises the polynucleotide SEQ ID NO:13 (Rouviere, P. E. et. al. EMBO J. (1995) 14:1032–1042 and Raina, S. et. al. EMBO J. (1995) 14:1043–1055);

8. RNA polymerase sigma factor H comprises the amino acid sequence of SEQ ID NO:16 and is encoded by a rpoH gene comprising SEQ ID NO:15 (Grossman, A. D. et. al. Cell (1984) 38:383–390);

9. RNA polymerase sigma factor N comprises the amino acid sequence of SEQ ID NO:18 and is encoded by a rpoN gene comprising SEQ ID NO:17 (Cannon, W. et. al. Mol. Microbiol. (1996) 21:233–245);

10. Chaperone protein DnaK comprises the amino acid sequence of SEQ ID NO:20 and is encoded by a dnaK gene comprising SEQ ID NO:19 (Zylicz, M. and Georgopoulos, C. J. Biol. Chem. (1984) 259:8820–8825);

11. Chaperone protein DnaJ comprises the amino acid sequence of SEQ ID NO:22 and is encoded by a dnaJ gene comprising SEQ ID NO:21 (Zylicz, M. et. al. J. Biol. Chem. (1985) 260:7591–7598);

12. Chaperone protein HscA comprises the amino acid sequence of SEQ ID NO:24 and is encoded by a hscA gene comprising SEQ ID NO:23 (The activity of chaperone protein HscA and HscB can be assayed as ATP hydrolysis activity (Vickery, L. E., Protein Sci. (1997) 6:1047–1056) and as inhibitory activity to protein denaturation (Silberg, J. J., J. Bacteriol. (1998) 180:6617–6624));

13. Chaperone protein HscB comprises the amino acid sequence of SEQ ID NO:26 and is encoded by a hscB gene comprising SEQ ID NO:25 (The activity of chaperone protein HscA and HscB can be assayed as ATP hydrolysis activity (Vickery, L. E., Protein Sci. (1997) 6:1047–1056) and as inhibitory activity to protein denaturation (Silberg, J. J., J. Bacteriol. (1998) 180:6617–6624));
14. Chaperone protein GroEL1 comprises the amino acid sequence of SEQ ID NO:28 and is encoded by a groEL1 gene comprising SEQ ID NO:27 (The activity of GroEL can be detected as ATP hydrolysis activity (Terlesky, K. C. and Tabita, F. R., Biochemistry (1991) 30:8181–8186));
15. Chaperone protein GroES1 comprises the amino acid sequence of SEQ ID NO:30 and is encoded by a groES1 gene comprising SEQ ID NO:29 (The activity of GroES can be detected as inhibitory activity to the GroEL ATP hydrolysis activity (Terlesky, K. C. and Tabita, F. R., Biochemistry (1991) 30:8181–8186));
16. Chaperone protein GroEL2 comprises the amino acid sequence of SEQ ID NO:32 and is encoded by a groEL2 gene comprising SEQ ID NO:31 (The activity of GroEL can be detected as ATP hydrolysis activity (Terlesky, K. C. and Tabita, F. R., Biochemistry (1991) 30:8181–8186));
17. Chaperone protein GroES2 comprises the amino acid sequence of SEQ ID NO:34 and is encoded by a groES2 gene comprising SEQ ID NO:33 (The activity of GroES can be detected as inhibitory activity to the GroEL ATP hydrolysis activity (Terlesky, K. C. and Tabita, F. R., Biochemistry (1991) 30:8181–8186)).

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl (Anal. Biochem., 138:267–284, 1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C.

Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

Stringent hybridization conditions are understood to mean those conditions where hybridization, either in solution or on a solid support, occur between two polynucleotide molecules which are 70% to 100% homologous in nucleotide sequence which include 75%, 80%, 85%, 90%, 95%, 98% and all values and subranges therebetween.

Homology, sequence similarity or sequence identity of nucleotide or amino acid sequences may be determined conventionally by using known software or computer programs. To find the best segment of identity or similarity of sequences, BLAST (Altschul et al (1990) J. Mol. Biol. 215:403–410 and Lipman et al (1990) J. Mol. Biol. 215: 403–410), FASTA (Lipman et al (1985) Science 227:1435–1441), or Smith and Waterman (Smith and Waterman (1981) J. Mol. Biol. 147:195–197) homology search programs can be used. To perform global alignments, sequence alignment programs such as the CLUSTAL W (Thompson et al (1994) Nucleic Acids Research 22:4673–4680) can be used.

The present invention also provides processes for preparing amino acids using bacteria that comprise at least one polynucleotide whose expression is enhanced or attenuated. Likewise, the invention also provides processes for preparing amino acids using bacteria that comprise at least on polypeptide whose activity is enhanced or attenuated. Preferably, a bacterial cell with enhanced or attenuated expression of one or more of the polypeptides and/or polynucleotides described herein will improve amino acid yield at least 1% compared to a bacterial strain not having the enhanced or attenuated expression. For the production of amino acids the *M. methylotrophus* polynucleotides described herein may be used to target expression, either by disruption to turn off or increase or enhance the expression or relative activity of the polypeptide enzymes encoded therein.

The term "enhancement" as used herein means increasing intracellular activity of one or more polypeptides in the bacterial cell, which in turn are encoded by the corresponding polynucleotides described herein. To facilitate such an increase, the copy number of the genes corresponding to the polynucleotides described herein may be increased. Alternatively, a strong and/or inducible promoter may be used to direct the expression of the polynucleotide, the polynucleotide being expressed either as a transient expression vehicle or homologously or heterologously incorporated into the bacterial genome. In another embodiment, the promoter, regulatory region and/or the ribosome binding site upstream of the gene can be altered to achieve the over-expression. The expression may also be enhanced by increasing the relative half-life of the messenger RNA.

In another embodiment, the enzymatic activity of the polypeptide itself may be increased by employing one or more mutations in the polypeptide amino acid sequence, which increases the activity. For example, altering the relative Km of the polypeptide with its corresponding substrate will result in enhanced activity. Likewise, the relative half-life of the polypeptide may be increased.

In either scenario, that being enhanced gene expression or enhanced enzymatic activity, the enhancement may be achieved by altering the composition of the cell culture media and/or methods used for culturing.

"Enhanced expression" or "enhanced activity" as used herein means an increase of at least 10%, 25%, 50%, 75%, 100%, 150%, 200%, 300%, 400% or 500% compared to a wild-type protein, polynucleotide, gene; or the activity and/or the concentration of the protein present before the polynucleotides or polypeptides are enhanced.

The term "attenuation" as used herein means a reduction or elimination of the intracellular activity of the polypeptides in a bacterial cell that are encoded by the corresponding polynucleotide. To facilitate such a reduction or elimination, the copy number of the genes corresponding to the polynucleotides described herein may be decreased or removed. Alternatively, a weak and/or inducible promoter may used to direct the expression of the polynucleotide, the polynucleotide being expressed either as a transient expression vehicle or homologously or heterologously incorporated into the bacterial genome. For example, the endogenous promoter or regulatory region of the gene corresponding to the isolated polynucleotides described herein may be replaced with the aforementioned weak and/or inducible promoter. Alternatively, the promoter or regulatory region may be removed. The expression may also be attenuated by decreasing the relative half-life of the messenger RNA.

In another embodiment, the enzymatic activity of the polypeptide itself may be decreased or deleted by employing one or more mutations in the polypeptide amino acid sequence, which decreases the activity or removes any detectable activity. For example, altering the relative Kd of the polypeptide with its corresponding substrate will result in attenuated activity. Likewise, a decrease in the relative half-life of the polypeptide will result in attenuated activity.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

Suitable vectors for carrying *M. methylotrophus* polynucleotides include those vectors which can direct expression of the gene in bacterial cells as known in the art. One embodiment of the present invention is whereby the vectors contain an inducible or otherwise regulated expression system whereby the *M. methylotrophus* polynucleotides may be expressed under certain conditions and not expressed under other conditions. Furthermore, in another embodiment of the invention, the *M. methylotrophus* polynucleotides can be constitutively expressed. Examples of such vectors and suitable cells in which they can be introduced are described in Sambrook et al., Molecular Cloning: A Laboratory Manual, 3rd Ed., Cold Spring Harbor Laboratory Press, Cold Spring Harbor, N.Y. (2001) and Current Protocols in Molecular Biology, Ausebel et al, (Eds.), John Wiley and Sons, Inc., New York, 2000.

Methods of introducing *M. methylotrophus* polynucleotides or vectors containing the *M. methylotrophus* polynucleotides include electroporation, conjugation, calcium-mediated transfection, infection with bacteriophage and other methods known in the art. These and other methods are described in Sambrook et al., Molecular Cloning: A Laboratory Manual, 3rd Ed., Cold Spring Harbor Laboratory Press, Cold Spring Harbor, N.Y. (2001) and Current Protocols in Molecular Biology, Ausebel et al, (Eds.), John Wiley and Sons, Inc., New York (2000).

The microorganisms that can be used in the present invention should have the ability to produce amino acids, preferably L-amino acids, from a suitable carbon source, preferably carbon sources such as methanol, glucose, sucrose, lactose, fructose, maltose, molasses, starch, cellulose glycerol or ethanol. The microorganisms can be Methylophilus bacteria, preferably *Methylophilus methylotrophus*.

Suitable culture conditions for the growth and/or production of *M. methylotrophus* polynucleotides are dependent on the cell type used. Likewise, culturing cells that contain attenuated or enhanced expression of the *M. methylotrophus* polynucleotides or polypeptides, as described herein, may be cultured in accordance with methods known in the art. Examples of culture conditions for various cells is described in Sambrook et al., Molecular Cloning: A Laboratory Manual, 3rd Ed., Cold Spring Harbor Laboratory Press, Cold Spring Harbor, N.Y. (2001); Current Protocols in Molecular Biology, Ausebel et al, (Eds.), John Wiley and Sons, Inc., 2000; and Cells: A Laboratory Manual (Vols. 1–3), Spector et al, (Eds.), Cold Spring Harbor Laboratory Press, Cold Spring Harbor, N.Y., (1988).

Following culturing the polypeptide or protein products, which are encoded by the *M. methylotrophus* polynucleotides, may be purified using known methods of protein purification. These methods include high performance liquid chromatography (HPLC), ion-exchange chromatography, size exclusion chromatography; affinity separations using materials such as beads with exposed heparin, metals, or lipids; or other approaches known to those skilled in the art. These and other methods of protein purification are disclosed in Sambrook et al., Molecular Cloning: A Laboratory Manual, 3rd Ed., Cold Spring Harbor Laboratory Press, Cold Spring Harbor, N.Y. (2001); Current Protocols in Molecular Biology, Ausebel et al, eds., John Wiley and Sons, Inc., 2000 and Protein Purification, Scopes and Cantor, (Eds.), Springer-Verlag, (1994). Likewise, the amino acids produced may be purified by methods known in the art using similar chromatography devices.

The invention also provides antibodies that bind to the polypeptides of the present invention. Antibodies binding to the polypeptides can be either monoclonal or polyclonal, preferably the antibodies are monoclonal. Methods for obtaining antibodies that bind to the polypeptides are known in the art and are described, for example, in Harlow and Lane, Antibodies: A Laboratory Manual, Cold Spring Harbor Laboratory Press, Cold Spring Harbor, N.Y. (1988).

Having generally described this invention, a further understanding can be obtained by reference to certain specific examples which are provided herein for purposes of illustration only, and are not intended to be limiting unless otherwise specified.

EXAMPLES

Whole genome sequencing using random shotgun method is described in Fleischman R. D. et. al. (1995) Science, 269: 496–512.

Example 1

Construction of Genomic Libraries of *Methylophilus methylotrophus*

*M. methylotrophus* AS1 was cultured at 30° C. in the 121 medium described in the Catalogue of Strains (The National Collections of Industrial and Marine Bacteria Ltd., 1994).

Cells were collected by centrifugation. Genomic DNA was isolated using the Genome-tip system (Qiagen K. K., Tokyo, Japan). The genomic DNA was sheared and fragmentized by sonication. The resultant fragments in the 1- to 2-kb size range were purified by gel electrophoresis through 1% low-melting agarose gel, followed by recovery using the Wizard DNA purification kit (Promega KK, Tokyo, Japan). The recovered fragments were ligated to the high-copy number vector pUC118 treated by HincII and bacterial alkaline phosphatase (Takara Shuzo, Kyoto, Japan), and this was designated pUC118 library.

For larger fragments (9- to 11-kb in size), the genomic DNA was partially digested by restriction endonuclease Sau3AI, followed by 0.6% agarose gel electrophoresis. The DNA fragments corresponding 9-kb to 11-kb in size were excised from gel and were recovered using the DNACELL (Daiichi Pure Chemicals, Tokyo, Japan). The recovered fragments were ligated into the low-coy number vector pMW118 (Nippon Gene, Toyama, Japan), which is a derivative of the pSC101 (Bernaidi, A. and Bernardi, F. (1984) Nucleic Acids Res. 12, 9415–9426). This library composed of large DNA fragments was designated pMW118 library.

General DNA manipulation was performed according to previously described methods (Sambrook et. al. (1989) "Molecular Cloning: A Laboratory Manual/Second Edition", Cold Spring Harbor Laboratory Press).

Example 2

DNA Sequencing and Sequence Assembly

The pUC118 library were transformed into *Escherichia coli* DH5α and plated on Luria-Bertani medium containing 100 μg/ml ampicillin and 40 μg/ml 5-bromo-4-chloro-3-indolyl-α-D-galactoside (X-Gal). The white colonies were picked up and cultured in Luria-Bertani medium containing 100 μg/ml ampicillin. The individual colony was cultured in the well of the 96 deep-well plates, and the plasmids were isolated using QIAprep Turbo Kit (Qiagen). The DNA fragments inserted into pUC118 were sequenced using a M13 reverse primer. The shotgun sequencing was performed with the BigDye terminators and 3700 DNA analyzer (Applied Biosystems Japan, Tokyo, Japan). Approximately 50,000 samples from pUC118 library corresponding to coverage of approximately 8-fold to the genome size were analyzed and the sequences were assembled by Phred/Phrap software (CodonCode, MA, USA). This assembly treatment yielded 60 contigs with more than 5 kb in size.

As for pMW118 library, 2,000 clones corresponding to coverage of approximately 5-fold were sequenced using both M13 forward and reverse primers. The end-sequence data were analyzed and the linking clones between contigs were selected from pMW118 library. The inserted fragments of selected clones were amplified by the polymerase chain reaction (PCR) using LA Taq polymerase (Takara Shuzo) and *M. methylotrophus* genomic DNA as a template. These products of PCR were entirely sequenced as described in Example 1, and the gap DNA sequences between contigs were determined. By the additional sequence information, the Phrap assembly software reduced the number of contigs with more than 5 kb in size to 24. Then the 48 DNA primers with sequences complementary to the end-sequences of the 24 contigs were prepared. All possible pairwise combination of the primers were tested by PCR to amplify the DNA fragments of *M. methylotrophus* genomic DNA. The amplified products were sequenced directly. In several cases, the additional primers complementary to different sequences at the end of the contig were used. This strategy could close all of the remaining physical gaps and resulted in a single circular contig. Several regions that had been sequenced in only one direction and had postulated secondary structure were confirmed. By this research, the genome of *M. methylotrophus* was found to be a single circular with the size of 2,869,603 bases and GC content of 49.6%.

Example 3

Sequence Analysis and Annotation

Sequence analysis and annotation was managed using the Genome Gambler software (Sakiyama, T. et. al. (2000) Biosci. Biotechnol. Biochem. 64: 670–673). All open reading frames of more than 150 bp in length were extracted and the translated amino acid sequences were searched against non-redundant protein sequences in GenBank using the BLAST program (Altschul, S. F. et. al. (1990) J. Mol. Biol. 215, 403–410). Of putative polynucleotide encoding sequences with significant similarities to the sequences in public databases (BLASTP scores of more than 100), the genes involved in biosynthesis of amino acids were selected. Start codons (AUG or GUG) were putatively identified by similarity of the genes and their proximity to the ribosome binding sequences (Shine, J. and Dalgarno, L. (1975) Eur. J. Biochem. 57: 221–230). Careful assignment of gene function resulted in the identification of the recombination protein genes (recR, recN, and recO), integration host factor genes (infA, and infB), and RNA polymerase sigma factor genes (rpoD, rpoE, rpoH, and rpoN). Also, chaperone proteins genes (dank, dnaJ, hscA, hscB, groEL, and groES) were identified. Two pairs of chaperone protein genes, dnaK-dnaJ and hscA-hscB were found in a putative operon, respectively. On the other hand, 2 copies chaperone protein genes groEL-groES were found in the genome. Therefore we designated them as groEL1-groES1 and groEL2-groES2.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide encoding a protein comprising the amino acid sequence of SEQ ID NO:16.

2. A vector comprising the isolated polynucleotide of claim 1.

3. A host cell comprising the isolated polynucleotide of claim 1.

4. The host cell of claim 3, which is a *Methylophilus* bacterium.

5. The host cell of claim 4, which is a *Merhylophilus methylotrophus* bacterium.

6. A method of making a protein comprising:
culturing the host cell of claim 3 for a time and under conditions suitable for expression of the protein; and
collecting said protein.

7. An isolated polynucleotide comprising the nucleotide sequence of SEQ ID NO:15.

8. A vector comprising the isolated polynucleotide of claim 7.

9. A host cell comprising the isolated polynucleotide of claim 7.

10. The host cell of claim 9, which is a *Methylophilus* bacterium.

11. The host cell of claim 10, which is a *Methylophilus methylotrophus* bacterium.

12. A method for making a protein comprising:
culturing the host cell of claim 9 for a time and under conditions suitable for the expression of the polynucleotide to produce a protein; and
collecting said protein.

13. An isolated polynucleotide, which hybridizes under high stringent conditions to the isolated polynucleotide of claim 7, wherein said high stringent conditions are hybridization in 50% formamide, 1 M NaCl, 1% SDS at 37° C., and a wash in 0.1 ×SSC at 60° C. to 65° C., and wherein said polynucleotide encodes a protein having sigma factor H activity.

14. A vector comprising the isolated polynucleotide of claim 13.

15. A host cell comprising the isolated polynucleotide of claim 13.

16. A method of making a protein comprising:
culturing the host cell of claim 15 for a time and under conditions suitable for the expression of the polynucleotide to produce a protein; and
collecting said protein.

17. An isolated polynucleotide, which is at least 95% identical to the polynucleotide of claim 7, and wherein said polynucleotide encodes a protein having sigma factor H activity.

18. A vector comprising the isolated polynucleotide of claim 17.

19. A host cell comprising the isolated polynucleotide of claim 17.

20. A method of making a protein comprising:
culturing the host cell of claim 19 for a time and under conditions suitable for the expression of the polynucleotide to produce a protein; and
collecting said protein.

* * * * *